US008465925B2

(12) United States Patent
Dapprich et al.

(10) Patent No.: US 8,465,925 B2
(45) Date of Patent: Jun. 18, 2013

(54) METHOD FOR NUCLEIC ACID ISOLATION AND AMPLIFICATION

(75) Inventors: Johannes Dapprich, Lawrenceville, NJ (US); Nancy Murphy, Downingtown, PA (US); Christian Korfhage, Langenfeld (DE)

(73) Assignees: Generation Biotech, LLC, Lawrenceville, NJ (US); GenoVision Inc., West Chester, PA (US); QIAGEN GmbH, Hilden (DE)

( * ) Notice: Subject to any disclaimer, the term of this patent is extended or adjusted under 35 U.S.C. 154(b) by 876 days.

(21) Appl. No.: 12/098,197

(22) Filed: Apr. 4, 2008

(65) Prior Publication Data

US 2009/0047674 A1 Feb. 19, 2009

Related U.S. Application Data

(63) Continuation of application No. 11/199,818, filed on Aug. 9, 2005, now abandoned.

(60) Provisional application No. 60/599,903, filed on Aug. 9, 2004.

(51) Int. Cl.
*C12Q 1/68* (2006.01)
*C12P 19/34* (2006.01)

(52) U.S. Cl.
USPC ............................ 435/6.12; 435/6.1; 435/6.11

(58) Field of Classification Search
None
See application file for complete search history.

(56) References Cited

U.S. PATENT DOCUMENTS

| | | | |
|---|---|---|---|
| 4,762,779 A | 8/1988 | Snitman | |
| 4,888,274 A | 12/1989 | Radding et al. | |
| 5,387,510 A | 2/1995 | Wu | |
| 5,547,843 A | 8/1996 | Studier et al. | |
| 5,665,582 A | 9/1997 | Kausch et al. | |
| 5,731,153 A | 3/1998 | Lucas et al. | |
| 5,759,773 A | 6/1998 | Tyagi et al. | |
| 5,856,092 A | 1/1999 | Dale et al. | |
| 5,858,671 A | 1/1999 | Jones | |
| 5,876,936 A | 3/1999 | Ju | |
| 5,939,261 A | 8/1999 | Loewy et al. | |
| 5,952,174 A | 9/1999 | Nikiforov et al. | |
| 6,004,744 A | 12/1999 | Goelet et al. | |
| 6,013,431 A | 1/2000 | Söderlund et al. | |
| 6,124,092 A | 9/2000 | O'Neill et al. | |
| 6,124,120 A * | 9/2000 | Lizardi ........................ 435/91.2 |
| 6,140,489 A | 10/2000 | Brenner | |
| 6,221,581 B1 | 4/2001 | Engelhardt et al. | |
| 6,261,773 B1 | 7/2001 | Segawa et al. | |
| 6,268,147 B1 | 7/2001 | Beattie et al. | |
| 6,309,833 B1 | 10/2001 | Edman et al. | |
| 6,355,422 B1 * | 3/2002 | Liu et al. ........................ 435/6 |
| 6,482,592 B1 | 11/2002 | Lundeberg et al. | |
| 6,844,154 B2 | 1/2005 | Landers | |
| 2001/0031467 A1 | 10/2001 | Dapprich et al. | |
| 2005/0221341 A1 * | 10/2005 | Shimkets et al. ................. 435/6 |

FOREIGN PATENT DOCUMENTS

| | | |
|---|---|---|
| WO | WO 90/01563 A1 | 2/1990 |
| WO | WO 94/01447 A1 | 1/1994 |
| WO | WO 95/00669 A1 | 1/1995 |
| WO | WO 97/42345 A1 | 11/1997 |
| WO | WO 98/26095 A1 | 6/1998 |
| WO | WO 00/56925 A2 | 9/2000 |
| WO | WO 01/42510 A3 | 6/2001 |
| WO | WO 01/90419 A2 | 11/2001 |

OTHER PUBLICATIONS

Loeffler et al., "Development and evaluation of the Nuclisens Basic Kit NASBA for the detection of RNA from *Candida* species frequently resistant to antifungal drugs," Diagnostic Microbiology and Infectious Disease, 2003, vol. 45, pp. 217-220.*
Amersham Biosciences, "Amersham Biosciences Simplifies DNA preparation Process with Innovative Whole Genome Amplification," Business Wire, Apr. 2003, pp. 1-2 (http://findarticles.com/p/articles/mi_m0EIN/is_2003_April_10/ai_99853744).*
Antson, D.-O. et al., "PCR-generated padlock probes detect single nucleotide variation in genomic DNA," *Nucleic Acids Research*, 28(12):e58, i-vi, 2000.
Barre, F-X. et al., "Unambiguous demonstration of triple-helix-directed gene modification," PNAS, 97(7):3084-3088, Mar. 28, 2000.
Belotserkovskii, B. P. et al., "DNA Hybrids Stabilized by Heterologies," *Biochemistry*, 38(33):10785-10792, 1999.
Bradshaw, M. S. et al., "A long-range regulatory element of *Hoxc8* identified by using the pClasper vector," *Proc. Natl. Acad. Sci. USA*, 93:2426-2430, Mar. 1996.
Bradshaw, M. S. et al., "A new vector for recombination-based cloning of large DNA fragments from yeast artificial chromosomes," *Nucleic Acids Research*, 23(23):4850-4856, 1995.
Bukanov, N. O. et al., "PD-loop: A complex of duplex DNA with an oligonucleotide," *Proc. Natl. Acad. Sci. USA*, 95:5516-5520, May 1998.
Carver, T. E., Jr. et al., "Proofreading DNA: Recognition of aberrant DNA termini by the Klenow fragment of DNA polymerase I," *Proc. Natl. Acad. Sci. USA*, 91:10670-10674, Oct. 1994.
Carver, T. E., Jr., and David P. Millar, "Recognition of Sequence-Directed DNA Structure by the Klenow Fragment of DNA Polymerase I," *Biochemistry*, 37(7):1898-1904, 1998.
Chen, Z-Y. and Zarbl, H., "A Nonradioactive, Allele-Specific Polymerase Chain Reaction for Reproducible Detection of Rare Mutations in Large Amounts of Genomic DNA: Application to Human k-*ras*," *Analytical Biochemistry*, 244:191-194, 1997.
Cimino, G. D. et al., "Psoralens as photoactive probes of nucleic acid structure and function: Organic chemistry, photochemistry, and biochemistry," *Ann. Rev. Biochem.*, 54:1151-1193, 1985.
Cunningham, R. P. et al., "Homologous Pairing and Topological Linkage of DNA Molecules by Combined Action of *E. coli* RecA Protein and Topoisomerase I," *Cell*, 24:213-223, Apr. 1981.

(Continued)

*Primary Examiner* — Young J Kim
(74) *Attorney, Agent, or Firm* — Seed IP Law Group PLLC

(57) ABSTRACT

The present invention provides methods and compositions for sequence-specific isolation of polynucleotide molecules from nucleic acid populations and subsequent amplification of isolated polynucleotide molecules or fragments thereof.

36 Claims, 11 Drawing Sheets

OTHER PUBLICATIONS

Dapprich, J. and Nicklaus, N., "DNA attachment to optically trapped beads in microstructures monitored by bead displacement," *Bioimaging*, 6:25-32, 1998.

Dapprich, J., "Single-Molecule DNA Digestion by Lambda-Exonuclease," *Cytometry*, 36:163-168, 1999.

Dapprich, J. et al., "Automated Haplotype-Specific Separation and Allele-Level Typing of Ambiguous Allele-Pairs," *Human Immunology*, 64(Suppl. 1):S90, 2003.

Davidson, S., "Research suggests importance of haplotypes over SNPs," *Nature Biotechnology*, 18:1134-1135, Nov. 2000.

Dawson, B. A. et al., "Affinity Isolation of Transcriptionally Active Murine Erythroleukemia Cell DNA Using a Cleavable Biotinylated Nucleotide Analog," *The Journal of Biological Chemistry*, 264(22):12830-12837, Aug. 5, 1989.

Detter, J. C. et al., "Isothermal Strand-Displacement Amplification Applications for High-Throughput Genomics," *Genomics*, 80(6):691-698, Dec. 2002.

Dieffenbach, C. W. et al., "General Concepts for PCR Primer Design," *PCR Primer—A Laboratory Manual*, Cold Spring Harbor Laboratory Press, pp. 133-142, 1995.

Drysdale, C. M. et al., "Complex promoter and coding region $\beta_2$-adrenergic receptor haplotypes alter receptor expression and predict in vivo responsiveness," *PNAS*, 97(19):10483-10488, Sep. 12, 2000.

Duhamel, R. C. and Whitehead, J. S., "Prevention of Nonspecific Binding of Avidin," *Methods in Enzymology*, 184:201-207, 1990.

Escudé, C. et al., "Padlock oligonucleotides for duplex DNA based on sequence-specific triple helix formation," *Proc. Natl. Acad. Sci. USA*, 96:10603-10607, Sep. 1999.

Francois, J-C. et al., "Sequence-specific recognition and cleavage of duplex DNA via triple-helix formation by oligonucleotides covalently linked to a phenanthroline-copper chelate," *Proc. Natl. Acad. Sci. USA*, 86:9702-9706, Dec. 1989.

Gurrieri, S. and Bustamante, C., "Purification and staining of intact yeast DNA chromosomes and real-time observation of their migration during gel electrophoresis," *Biochem. J.*, 326:131-138, 1997.

Gurrieri, S. et al, "Trapping of megabase-sized DNA molecules during agarose gel electrophoresis," *Proc. Natl. Acad. Sci. USA*, 96:453-458, Jan. 1999.

Hacia, J. G. et al., "Determination of ancestral alleles for human single-nucleotide polymorphisms using high-density oligonucleotide arrays," *Nature Genetics*, 22:164-167, Jun. 1999.

Hafner, G. J. et al., "Isothermal Amplification and Multimerization of DNA by Bst DNA Polymerase," *BioTechniques*, 30(4):852-867, Apr. 2001.

Hakvoort, T. B. M. et al., *Gene Cloning and Analysis by RT-PCR, Bio Techniques® Books (Division of Eaton Publishing)*, 1998, Chapter 19, "Enriched Full-Length cDNA Expression Library by RecA-Mediated Affinity Capture," pp. 259-269.

Hakvoort, T. B. M. et al., "Preparation of a differentially expressed, full-length cDNA expression library by RecA-mediated triple-strand formation with subtractively enriched cDNA fragments," *Nucleic Acids Research*, 24(17):3478-3480, 1996.

Hodge, S. et al., "Loss of information due to ambiguous haplotyping of SNPs," *Nature Genetics*, 21:360-361, Apr. 1999.

Honigberg, S. M. et al., "Ability of RecA protein to promote a search for rare sequences in duplex DNA," *Proc. Natl. Acad. Sci., USA*, 83:9586-9590, Dec. 1986.

Iyer, M. et al., "Accelerated Hybridization of Oligonucleotides to Duplex DNA," *The Journal of Biological Chemistry*, 270(24):14712-14717, Jun. 16, 1995.

Judson, R. et al., "The predictive power of haplotypes in clinical response," *Pharmacogenomics*, 1(1):15-26, 2000.

Kwok, S. et al., "Design and Use of Mismatched and Degenerate Primers," *PCR Primer—A Laboratory Manual*, Cold Spring Harbor Laboratory Press, pp. 143-155, 1995.

Le Doan, T. et al., "Recognition and Photo-Induced Cleavage and Cross-Linking of Nucleic Acids by Oligonucleotides Covalently Linked to Ellipticine," *Antisense Research and Development*, 1:43-54, 1991.

Little, M. C. et al., "Isothermal Amplification of DNA Targets by Strand Displacement Amplification," *Nonradioactive Labeling and Detection of Biomolecules*, Chapter 16.3, pp. 218-223, 1992.

McCarthy, J. J. and Hilfiker, R., "The use of single-nucleotide polymorphism maps in pharmacogenomics," *Nature Biotechnology*, 18:505-508, May 2000.

Mitchell, L. G. and Merril, C. R., "Affinity Generation of Single-Stranded DNA for Dideoxy Sequencing following the Polymerase Chain Reaction," *Analytical Biochemistry*, 178:239-242, 1989.

Mitchell, L. G. et al., *Methods in Molecular Biology, Harwood Humana Press Inc.*, Totowa, NJ, 1996, vol. 58, Chapter 14. "Use of Silver Staining to Detect Nucleic Acids," pp. 97-103.

Mitra, R. D. and Church, G. M., "In situ localized amplification and contact replication of many individual DNA molecules," *Nucleic Acids Research*, 27(24):e34, i-iv, 1999.

Nelson, J. R. et al., "TempliPhi, φ29 DNA Polymerase Based Rolling Circle Amplification of Templates for DNA Sequencing," *BioTechniques*, 32:S44-S47, Jun. 2002.

Nilsson, M. et al., "Padlock probes reveal single-nucleotide differences, parent of origin and in situ distribution of centromeric sequences in human chromosomes 13 and 21," *Nature Genetics*, 16:252-255, Jul. 1997.

Perrino, F. W. et al., "Extension of mismatched 3' termini of DNA is a major determinant of the infidelity of human immunodeficiency virus type 1 reverse transcriptase," *Proc. Natl. Acad. Sci. USA*, 86:8343-8347, Nov. 1989.

Perrouault, L. et al., "Sequence-specific artificial photo-induced endonucleases based on triple helix-forming oligonucleotides," *Nature*, 344:358-360, Mar. 22, 1990.

Pfannschmidt, C. et al., "Sequence-specific labeling of superhelical DNA by triple helix formation and psoralen crosslinking," Nucleic Acids Research, 24(9):1702-1709, 1996.

Rigas, B. et al., "Rapid plasmid library screening using RecA-coated biotinylated probes," *Proc. Natl. Acad. Sci. USA*, 83:9591-9595, Dec. 1986.

Ruano, G. et al., "Haplotype of multiple polymorphisms resolved by enzymatic amplification of single DNA molecules," *Proc. Natl. Acad. Sci. USA*, 87:6296-6300, Aug. 1990.

Ryan, D. et al., "Non-PCR-Dependent Detection of the Factor V Leiden Mutation From Genomic DNA Using a Homogeneous Invader Microtiter Plate Assay," *Molecular Diagnosis*, 4(2):135-144, 1999.

Sayers, J. R. et al., "Strand specific cleavage of phosphorothioate-containing DNA by reaction with restriction endonucleases in the presence of ethidium bromide," *Nucleic Acids Research*, 16(3):803-814, 1988.

Sayers, J. R. et al., "5'—3' Exonucleases in phosphorothioate-based oligonucleotide-directed mutagenesis," *Nucleic Acids Research*, 16(3):791-802, 1988.

Sena, E. P. and Zarling, D. A., "Targeting in linear DNA duplexes with two complementary probe strands for hybrid stability," *Nature Genetics*, 3:365-372, Apr. 1993.

Sobel, E. and Lange, K., "Descent Graphs in Pedigree Analysis: Applications to Haplotyping, Location Scores, and Marker-Sharing Statistics," *Am. J. Human Genet.*, 58(6):1323-1337, 1996.

Stahl, S. et al., "Solid phase DNA sequencing using the biotin—avidin system," *Nucleic Acids Research*, 16(7):3025-3038, 1988.

Stephens, J. C. et al., "Haplotype Variation and Linkage Disequilibrium in 313 Human Genes," *Science*, 293:489-493, Jul. 20, 2001.

Sun, J-S. et al., "Sequence-specific intercalating agents: Intercalation at specific sequences on duplex DNA via major groove recognition by oligonucleotide-intercalator conjugates," *Proc. Natl. Acad. Sci. USA*, 86:9198-9202, Dec. 1989.

Syvänen, A-C. et al., "Enthusiasm mixed with scepticism about single-nucleotide polymorphism markers for dissecting complex disorders," *European Journal of Human Genetics*, 7:98-101, 1999.

Tagle, D. A. et al., "Magnetic bead capture of expressed sequences encoded within large genomic segments," *Nature*, 361:751-753, Feb. 25, 1993.

Takasugi, M. et al., "Sequence-specific photo-induced cross-linking of the two strands of double-helical Dna by a psoralen covalently linked to a triple helix-forming oligonucleotide," *Proc. Natl. Acad. Sci. USA*, 88:5602-5606, Jul. 1991.

Teintze, M. et al., "RecA-Assisted Rapid Enrichment of Specific Clones From Model DNA Libraries," *Biochemical and Biophysical Research Communications*, 211(3):804-811, Jun. 26, 1995.

Tishkoff, S. A. et al., "The Accuracy of Statistical Methods for Estimation of Haplotype Frequencies: An Example from the CD4 Locus," *Am. J. Human Genetics*, 67:518-522, 2000.

Turino, C. et al., "Amplification of Haplo-Separated Genomic DNA by Haplotype-Specific Extraction (HSE) and Whole-Genome Amplification (WGA)," *Genes and Immunity*, 5(Suppl. 1):567, May 2004.

Turino, C. et al., "Amplification of Haplo-Separated Genomic DNA by Haplotype-Specific Extraction (HSE) and Whole-Genome Amplification (WGA)," *Human Immunology*, 65(Suppl. 1):S25, 2004.

Welcher, A. A. et al., "Selective enrichment of specific DNA, cDNA and RNA sequences using biotinylated probes, avidin and copper-chelate agarose," *Nucleic Acids Research*, 14(24):10027-10044, 1986.

Woolley, A. T. et al., "Direct haplotyping of kilobase-size DNA using carbon nanotube probes," *Nature Biotechnology*, 18:760-763, Jul. 2000.

Yan, H. et al., "Conversion of diploidy to haploidy," *Nature*, 403:723-724, Feb. 17, 2000.

Zenkova, M. et al., "A novel approach to introduce site-directed specific cross-links within RNA-protein complexes," *Eur. J. Biochem.*, 231(3):726-735, Aug. 1, 1995.

Zhumabayeva, B. et al., "ClonCapture™ cDNA Selection: A New Approach for the Simultaneous Cloning of Multiple Genes," *CLONTECHniques*, pp. 33-34, Oct. 1999.

Dynabeads® M-280 Streptavidin—Package Insert, *Dynal Biotech ASA*, Oslo, Norway, 2005, http://www.dynal.no/kunder\dynal\dynalpub.

*AmpliTaq*® DNA Polymerase, Applied Biosystems, 2006, Downloaded Apr. 25, 2006. https://products.appliedbiosystems.com/ab/en/US/adirect/ab?cmd=catNavigate2&catID=601622&tab=De . . . .

Detection Using Avidin-Biotin Systems "Signal Amplification Methods using Avidin-Biotin Chemistry," *Pierce Chemical Technical Library, Avidin-Biotin Chemistry: A Handbook*, pp. 227-230, Jan. 1992.

TechNote #303, "Lateral Flow Tests," *Bangs Laboratories, Inc.*, Rev. #001, pp. 1-6, Active Aug. 27, 1999.

Lin et al., "Nucleotide Sequence and Expression of *kerA*, the Gene Encoding a Keratinolytic Protease of *Bacillus licheniformis* PWD-1," *Applied and Environmental Microbiology*, 61 (4): 1469-1474, 1995.

Parker et al., "Targeted gene walking polymerase chain reaction," *Nucleic Acids Research*, 19 (11): 3055-3060, 1991.

Dapprich, J. et al., "Haploseparation and amplification of genomic DNA by haplotype-specific extraction (HSE) and whole-genome amplification (WGA)," (Abstract) *37th Annual Oak Ridge Conference: Pushing the Technology Envelope II: An Exploration of the Future of Clinical Laboratory Testing*, Hyatt Regency Inner Harbor, Baltimore, Maryland, Apr. 14-15, 2005.

Dapprich, J. et al., "Haploseparation and amplification of genomic DNA by haplotype-specific extraction (HSE) and whole-genome amplification (WGA)," (Poster) *37th Annual Oak Ridge Conference: Pushing the Technology Envelope II: An Exploration of the Future of Clinical Laboratory Testing*, Hyatt Regency Inner Harbor, Baltimore, Maryland, Apr. 14-15, 2005.

Dapprich, Johannes et al., "Multiplexed Haploseparation of Genomic DNA for HLA-A, HLA-B and HLA-DRB1 by Haplotype-Specific Extraction (HSE)," (Abstract) *ASHI 31st Annual Meeting*, Washington, D.C., Oct. 17-21, 2005.

Rook, Martha S., et al., "Technical Advance: Whole Genome Amplification of DNA from Laser Capture-Microdissected Tissue for High-Throughput Single Nucleotide Polymorphism and Short Tandem Repeat Genotyping," *American Journal of Pathology 164*(1):23-33, Jan. 2004.

\* cited by examiner

Haploid sequences can be assembled over arbitrary distances using overlapping heterozygous sites:

METHOD FOR NUCLEIC ACID ISOLATION AND AMPLIFICATION

CROSS REFERENCE TO RELATED APPLICATION

This application is a continuation of U.S. patent application Ser. No. 11/199,818, filed Aug. 9, 2005, now pending, which application claims the benefit of U.S. Provisional Patent Application No. 60/599,903, filed Aug. 9, 2004, where these applications are incorporated herein by reference in their entireties.

STATEMENT OF GOVERNMENT INTEREST

This invention was made with U.S. government support under NIH/NIAID grant numbers 1 R43 AI 51036-01 A2 and 2 R44 AI 51036-02. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025_414C1a_SEQUENCE_LISTING.txt. The text file is 2 KB, was created on Oct. 7, 2008, and is being submitted electronically via EFS-Web.

BACKGROUND

1. Technical Field

The invention relates generally to methods and compositions for isolating and amplifying nucleic acid molecules.

2. Description of the Related Art

One major area of current clinical research is the correlation of an individual's genetic profile to a susceptibility to disease and/or response to drug therapy. This area of research, which has been labeled pharmacogenomics, offers a strategy for targeting drugs to individuals, and for elucidating genetic predispositions and risks. In addition, pharmacogenomics provides for the possibility for an improved drug discovery process based on a better understanding of the molecular bases of complex diseases.

Identification of an individual's genetic profile can require the identification and amplification of particular nucleic acid sequences in the individual's genome. These particular nucleic acid sequences can include those that differ by one or a few nucleotides among individuals in the same species. For example, single-nucleotide polymorphisms (SNPs) are common variations in the DNA of individuals that are used to track inherited genetic patterns.

Current methods for isolating, amplifying and identifying nucleic acid polymorphisms can be labor-intensive, expensive, and not sensitive.

BRIEF SUMMARY

The present invention provides methods and compositions for isolating and amplifying nucleic acid molecules. A polynucleotide molecule of interest may be first isolated from other nucleic acid molecules in a nucleic acid population based on a specific sequence in the polynucleotide molecule and then isothermally amplified. In certain embodiments, the present invention allows for the isolation of relatively long polynucleotide molecules (e.g., about 50 kb or longer) and subsequent amplification of the isolated molecules or fragments thereof. The amplified polynucleotide molecules or fragments thereof may be further analyzed.

In one aspect, the present invention provides a method for amplifying a polynucleotide molecule of interest or a fragment thereof, comprising: (a) isolating a polynucleotide molecule from a nucleic acid population using an immobilizable separation group to provide an isolated polynucleotide molecule, and (b) isothermally amplifying the isolated polynucleotide molecule or a fragment thereof.

In certain embodiments, (A) the nucleic acid population comprises the polynucleotide molecule of interest, (B) one strand of the polynucleotide molecule comprises a target nucleic acid sequence and a distinguishing element, (C) the target nucleic acid sequence is within 100 nucleotides of the distinguishing element in the one strand of the polynucleotide molecules, and (D) step (a) comprises: (i) contacting the nucleic acid population with a targeting element that binds specifically to the target nucleic acid sequence in the polynucleotide molecule, (ii) selectively attaching the immobilizable separation group to the targeting element bound to the target nucleic acid sequence in the polynucleotide molecule to form a targeting element-separation group complex, (iii) immobilizing to a substrate via the separation group the targeting element-separation group complex to which the target nucleic acid sequence in the polynucleotide molecule is bound, and (iv) removing the immobilized targeting element-separation group complex to which the target nucleic acid sequence in the polynucleotide molecule is bound, thereby isolating the polynucleotide molecule from the nucleic acid population.

In certain embodiments, (1) the targeting element comprises an oligonucleotide, (2) the separation group comprises an immobilizable nucleotide, and (3) the separation group is attached to the targeting element by extending the oligonucleotide in the presence of the immobilizable nucleotide, thereby forming an extension product that comprises the immobilizable nucleotide.

In certain embodiments, (4) the 3' terminus of the oligonucleotide is complementary to the distinguishing element or a portion thereof in the polynucleotide molecule, (5) the immobilizable nucleotide is non-terminating, and (6) the extension product comprises multiple separation groups.

In certain other embodiments, (4) the target nucleic acid sequence is immediately 3' to the distinguishing element, and (5) the immobilizable nucleotide is terminating and complementary to the distinguishing element or a portion thereof.

In certain embodiments, (A) the nucleic acid population comprises the polynucleotide molecule of interest, (B) one strand of the polynucleotide molecule comprises a target nucleic acid sequence and a distinguishing element, (C) the target nucleic acid sequence is within 100 nucleotides of the distinguishing element in the one strand of the polynucleotide molecule, and (D) step (a) comprises: (i) contacting the nucleic acid population with a targeting element-separation group complex, wherein the targeting element-separation group complex binds specifically to the target nucleic acid sequence in the polynucleotide molecule, (ii) selectively stabilizing the binding of the targeting element-separation group complex to the target nucleic acid sequence in the polynucleotide molecule, (iii) immobilizing to a substrate via the separation group the stabilized targeting element-separation group complex to which the target nucleic acid sequence in the polynucleotide molecule is bound, and (iv) removing the immobilized stabilized targeting element-separation group complex to which the target nucleic acid sequence in the polynucleotide molecule is bound, thereby isolating the polynucleotide molecule from the nucleic acid population.

In certain embodiments, (1) the targeting element comprises an oligonucleotide, and (2) the 3' terminus of the oligonucleotide is complementary to the distinguishing element or a portion thereof in the polynucleotide.

In certain embodiments, the selective stabilization is performed by ligation. In certain other embodiments, the selective stabilization is performed by extension of the oligonucleotide using the polynucleotide molecule as a template.

In certain embodiments, step (b) is performed by strand displacement amplification.

In certain embodiments, step (b) is generic amplification. In certain other embodiments, step (b) is sequence-specific amplification (e.g., locus-specific amplification). In certain other embodiments, step (b) is sequence-biased amplification (e.g., locus-biased amplification).

In certain embodiments, step (b) amplifies all of the regions of the isolated polynucleotide molecule. In certain other embodiments, step (b) amplifies a particular region of the isolated polynucleotide molecule.

In certain embodiments, step (b) is performed in the presence of a first set of specific primers each of which is at least substantially complementary to the particular region in the strand of the polynucleotide molecule that comprises the target nucleic acid sequence.

In certain related embodiments, step (b) is performed further in the presence of a second set of specific primers each of which is at least substantially complementary to the particular region in the strand of the polynucleotide molecule that does not comprise the target nucleic acid sequence.

In certain embodiments, the first set of specific primers are about 0.5 kb apart from their neighboring primers when annealing to the strand of the isolated polynucleotide molecule that comprises the target nucleic acid sequence.

In certain embodiments, the second set of specific primers are about 0.5 kb apart from their neighboring primers when annealing to the strand of the isolated polynucleotide molecule that does not comprise the target nucleic acid sequence.

In certain embodiments, step (b) is performed further in the presence of a set of random primers. In certain embodiments, the random primers are about 2 kb apart from their neighboring primers.

In certain embodiments, step (b) is performed in the presence of end-specific primers. In certain embodiments, the average distance between neighboring end-specific primers are between 50 and 250 nucleotides.

In certain embodiments, step (b) is performed further in the presence of center-specific primers. In certain embodiments, the distances between neighboring center-specific primers are between 100 and 5000 nucleotides.

In certain embodiments, the center-specific primers are sequence-specific. In certain other embodiments, the center-specific primers are degenerate primers.

In certain embodiments, the method according to the present invention further comprises: (c) characterizing one or more sites in the amplified polynucleotide molecule or fragment thereof that constitute a haplotype. Such a method may further comprise: (d) assembling information of the characterized sites.

In certain related embodiments, the method according to the present invention further comprises: (c) characterizing one or more polymorphic sites in the amplified polynucleotide molecule or fragment thereof. Such a method may further comprise: (d) assembling information of the characterized sites to determine a haplotype.

In another aspect, the present invention provides a method for amplifying multiple polynucleotide molecules of interest from a population of nucleic acid molecules, comprising: (a) isolating multiple polynucleotide molecules from a nucleic acid population using one or more immobilizable separation groups to provide isolated polynucleotide molecules of interest, and (b) isothermally amplifying the isolated polynucleotide molecules or fragments thereof.

In certain embodiments of multiplexed nucleic acid isolation and amplification, step (a) comprises: (A) contacting a nucleic acid population that comprises multiple polynucleotide molecules of interest with multiple targeting elements so that each targeting element binds specifically to a target nucleic acid sequence of its corresponding polynucleotide molecule, wherein (i) the target nucleic acid sequence is located within 100 nucleotides of a distinguishing element in one strand of the polynucleotide molecule, and (ii) the distinguishing element distinguishes the polynucleotide molecule from another nucleic acid molecule that is nearly identical to the polynucleotide molecule, (B) selectively attaching separation groups to the multiple targeting elements bound to the target nucleic acid sequences of corresponding polynucleotide molecules to form targeting element-separation group complexes, (C) immobilizing to substrate(s) via the separation groups the targeting element-separation group complexes to which the target nucleic acid sequences in the polynucleotide molecules are bound, and (D) removing the immobilized targeting element-separation group molecules are bound to isolate the polynucleotide molecules from the population of nucleic acid molecules.

In certain embodiments of multiplexed nucleic acid isolation and amplification, step (a) comprises: (A) contacting a nucleic acid population that comprises multiple polynucleotide molecules of interest with multiple targeting elements to which separation groups are attached so that each targeting element binds specifically to a target nucleic acid sequence of its corresponding polynucleotide molecule, wherein (i) each target nucleic acid sequence is located within 100 nucleotides of the corresponding distinguishing element in one strand of the polynucleotide molecule, and (ii) each distinguishing element distinguishes a specific polynucleotide molecule from other nucleic acid molecules that are nearly identical to the polynucleotide molecule, (B) selectively stabilizing the binding of the targeting elements to the target nucleic acid sequences of their corresponding polynucleotide molecules to form stabilized targeting element-separation group complexes to which the target nucleic acid sequences in the polynucleotide molecules are bound, (C) immobilizing to substrate(s) via the separation groups the targeting element-separation group complexes to which the target nucleic acid sequences in the polynucleotide molecules are bound, and (D) removing the immobilized targeting element-separation group complexes to which the target nucleic acid sequences in the polynucleotide molecules are bound to isolate the polynucleotide molecules from the population of nucleic acid molecules.

In certain embodiments, different separation groups are attached to different targeting elements. In certain other embodiments, identical separation groups are attached to different targeting elements.

In another aspect, the present invention provides a method for amplifying a genomic DNA molecule of interest or a fragment thereof, wherein the genomic DNA molecule of interest comprises a polymorphic sequence, comprising: (a) contacting a genomic DNA population that comprises the genomic DNA molecule of interest with an oligonucleotide, wherein (i) the oligonucleotide comprises a sequence at least substantially complementary to a target nucleic acid sequence in one strand of the genomic DNA molecule of interest, (ii) the target nucleic acid sequence is located immediately 3' to the polymorphic sequence in the one strand of the genomic DNA molecule of interest, and (iii) the 3' portion of the oligonucleotide is complementary to the polymorphic sequence or a portion thereof when annealing to the one strand of the genomic DNA molecule of interest, (b) extending the oligonucleotide in the presence of an immobilizable nucleotide using the one strand of the genomic DNA molecule of interest to which the oligonucleotide anneals as a template to provide an extension product, (c) immobilizing to a substrate via the immobilizable nucleotide the extension product to which the genomic DNA molecule of interest is bound, (d) removing the immobilized extension product to which the genomic DNA molecule of interest is bound to thereby isolate the genomic DNA molecule of interest from the genomic DNA population, (e) optionally elute the genomic DNA molecule of interest from the substrate, and (f) isothermally amplifying the isolated or eluted genomic DNA molecule of interest or a fragment thereof.

In another aspect, the present invention provides a method for assembling a haplotype comprising: (a) providing a nucleic acid population from an organism for which a haplotype is of interest; (b) separately isolating polynucleotide molecules by haplotype-specific extraction using multiple substrates, wherein (i) polynucleotide molecules are isolated at multiple extraction sites using each substrate, (ii) no polynucleotide molecules isolated at one extraction site using one substrate comprise a polymorphic site also present in polynucleotide molecules isolated at other extraction sites using the same substrate, (iii) one or more polynucleotide molecules isolated at one extraction site using one substrate comprise a polymorphic site also present in polynucleotide molecules isolated at a neighboring extraction site using other substrates, (c) separately characterizing polymorphic sites in polynucleotide molecules isolated using each substrate; (d) assembling a haplotype based on the characterization of polymorphic sites present in polynucleotide molecules isolated using more than one substrate.

In certain embodiments, the method for assembling a haplotype further comprises isothermally amplifying polynucleotide molecules isolated using the multiple substrates prior to step (c).

DETAILED DESCRIPTION

Figure 1A:
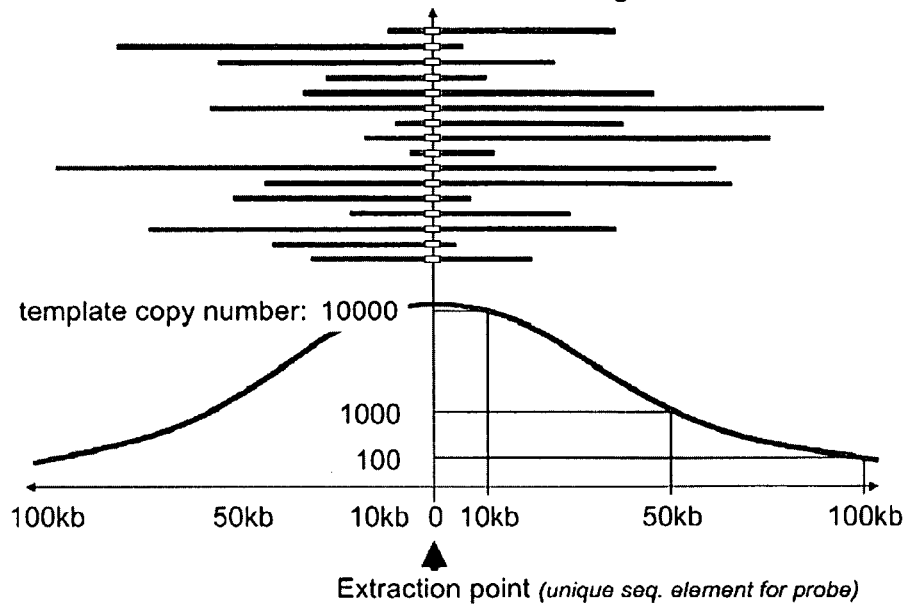
FIG. 1A is a graphical representation of the number of DNA molecules vs. length distribution for an isolated sample of nucleic acid molecules. Fragments are targeted at an extraction point characterized by a distinguishing element (in conjunction with a nearby or an overlapping target nucleic acid sequence) that uniquely identifies the fragments of interest. As an example, randomly sheared fragments will get captured along with any connected segments of the fragments that are located up- or down-stream of the extraction point, provided that they contain the unique sequence element (i.e., the distinguishing element in conjunction with a nearby or overlapping target nucleic acid sequence). The copy number of available captured templates for any given locus connected to the extraction point will decrease with increasing distance from the extraction point based on the overall size distribution of the fragments.

The present invention provides methods and compositions for isolating and amplifying nucleic acid molecules based on certain specific sequences (e.g., haplotype-specific or locus-specific) in the polynucleotide molecules. The isolated polynucleotide molecules may be subsequently isothermally amplified using generic, sequence-specific (e.g., locus-specific), or sequence-biased (e.g., locus-biased) amplification. In certain embodiments, the present invention is useful for isolating relatively large polynucleotide molecules (e.g., about 50 kb or longer) followed by amplifying the isolated polynucleotide molecules or portions thereof.

In certain embodiments, the methods according to the present invention have one or more of the following advantages: (1) facilitating the creation of haploid, re-usable genomic DNA libraries from existing DNA sources, (2) reducing complexity of nucleic acid analysis, thus increasing read-out sensitivity and resolution, (3) extending the directly achievable linkage distance per extraction and increasing the robustness of subsequent manipulations by increasing the amount of available template, (4) permitting the unambiguous typing of potentially difficult diploid samples with allele pair combinations that fail to be resolved by conventional sequence-based typing (SBT) or sequence-specific oligonucleotide probes (SSOP), and (5) allowing for typing of haplo-separated samples with multiple polymorphisms over large linkage distances.

The detailed description of the methods according to the present invention and their associated advantages are provided below:

A. Nucleic Acid Extraction

Sequence specific extraction is described generally in U.S. Patent Application Publication No. 20010031467 and PCT Application Publication No. WO 01/042150. In general, sequence specific extraction is a method for separating a polynucleotide molecule of interest from a population of nucleic acid molecules based on a specific sequence of the polynucleotide molecule of interest.

In certain embodiments, the nucleic acid extraction method comprises: (1) contacting a nucleotide acid population that comprises a polynucleotide molecule of interest with a targeting element, wherein (a) one strand of the polynucleotide molecule comprises a target nucleic acid sequence and a distinguishing element, (b) the target nucleic acid sequence is within 100 nucleotides of the distinguishing element in the one strand of the polynucleotide molecules, and (c) the targeting element binds specifically to the target nucleic acid sequence in the polynucleotide molecule of interest, (2) selectively attaching an immobilizable separation group to the targeting element bound to the target nucleic acid sequence in the polynucleotide molecule to form a targeting element-separation group complex, (3) immobilizing to a substrate via the separation group the targeting element-separation group complex to which the target nucleic acid sequence in the polynucleotide molecule is bound, and (4) removing the immobilized targeting element-separation group complex to which the target nucleic acid sequence in the polynucleotide molecule is bound, thereby isolating the polynucleotide molecule from the nucleic acid population.

In certain other embodiments, the nucleic acid extraction method comprises: (1) contacting a nucleotide acid population that comprises a polynucleotide molecule of interest with a targeting element-separation group complex, wherein (a) one strand of the polynucleotide molecule comprises a target nucleic acid sequence and a distinguishing element, (b) the target nucleic acid sequence is within 100 nucleotides of the distinguishing element in the one strand of the polynucleotide molecules, and (c) the targeting element-separation group complex binds specifically to the target nucleic acid sequence in the polynucleotide molecule of interest, (2) selectively stabilizing the binding of the targeting element-separation group complex to the target nucleic acid sequence in the polynucleotide molecule, (3) immobilizing to a substrate via the separation group the targeting element-separation group complex to which the target nucleic acid sequence in the polynucleotide molecule is bound, and (4) removing the immobilized stabilized targeting element-separation group complex to which the target nucleic acid sequence in the polynucleotide molecule is bound, thereby isolating the polynucleotide molecule from the nucleic acid population.

1. Sources of Nucleic Acids

Any nucleic acid specimen, in purified or non-purified form, can be utilized as the starting nucleic acid or acids, provided it contains, or is suspected of containing, a polynucleotide molecule of interest. Thus, the process may employ, for example, genomic DNA, plasmid DNA, amplified DNA, cDNA, total cellular RNA, hnRNA, and polyA-containing RNA. Nucleic acids can be from a single unicellular or eukaryotic organism. For example, the nucleic acid can be obtained from a mammalian organism such as a human. A mixture of nucleic acids may also be used.

The nucleic acid-containing sample may be from any source, including biological fluids or tissues (e.g., blood, serum, urine, stool, saliva, milk, ductal fluid, tears, buccal swap samples, and semen). The sample may alternatively be from an organ such as liver, brain, colon, urogenital, hematopoietic, thymus, testis, ovarian, uterine, prostate, breast, colon, lung and renal tissue, as well as a tumor associated with any of these tissues. Nucleic acid molecules can be extracted by a variety of techniques including those described by Sambrook and Russell (Molecular Cloning: A Laboratory Manual, Cold Spring Harbor, N.Y., $3^{rd}$ Ed. Pp 6.4-6.32, 6.63 and 6.64, 2001).

In general, nucleic acid populations directly isolated from biological samples may be used for sequence-specific extraction without being first amplified. Direct extraction without prior amplification (e.g., with random primers) may reduce background during extraction and subsequent amplification and analysis of the polynucleotide molecules of interest. However, if desired under certain circumstances, the population of nucleic acids can be amplified using PCR or another amplification technique, either in its entirety or selectively for the fragment(s) of interest, prior to performing sequence-specific extraction.

The sizes of nucleic acid molecules in a nucleic acid population depend on the source of the nucleic acid population (e.g., plasmid, viral genomes, bacterial genomes, eukaryotic genomes), the method used in preparing the population from a biological sample, and conditions under which the biological sample is stored prior to nucleic acid isolation. For example, fresh or well-stored samples generally contain less damaged nucleic acid molecules than those stored under non-conservative conditions or in samples that have been modified such as paraffin embedded tissues.

In certain embodiments where extraction and amplification of large polynucleotide molecules is desirable, methods for obtaining biological samples and subsequent nucleic acid isolation from such samples that maintain the integrity (i.e., minimize the breakage or shearing) of nucleic acid molecules are preferred. Exemplary methods include, but are not limited to, lysis methods without further purification (e.g., chemical or enzymatic lysis method using detergents, organic solvents, alkaline, and/or proteases), nuclei isolation with or without further nucleic acid purification, isolation methods using precipitation steps, nucleic acid isolation methods using solid matrices (e.g., silica-based membranes, beads, or modified surfaces that bind nucleic acid molecules), gel-like matrices (e.g., agarose) or viscous solutions, and methods that enrich nucleic acid molecules with a density gradient. In certain embodiments, prior to sequence-specific extraction of polynucleotide molecules of interest, isolated nucleic acid molecules may first be ligated to repair nicks generated during nucleic acid isolation, which in turn prevents single-stranded regions to fully denature and break into smaller fragments during optional denaturation steps of sequence-specific extraction. Exemplary methods for large polynucleotide isolation and purification may be found in Dear and Cook, Biochem J. 273 (Pt 3):695-9, 1991; Gurrieri and Bustamante, Biochem J. 326 (Pt 1):131-8, 1997; Upcroft and Upcroft, J Chromatogr. 618(1-2):79-93, 1993; Park et al., Clin Chem. 51(8):1520-3, 2005; Rook et al., Am J Pathol. 164(1):23-33, 2004; Hummelshoj et al., Biotechniques 38(4):605-10, 2005; Vester and Wengel, Biochemistry 43(42):13233-41, 2004; Dean et al., Proc Natl Acad Sci USA. 99(8):5261-6, 2002; Hosono et al., Genome Res. 13(5):954-64, 2003; and Kotler et al., Proc Natl Acad Sci USA. 90(9):4241-5, 1993.

2. Targeting

In certain embodiments, the isolation of a polynucleotide molecule of interest is based on a specific sequence (referred to herein as a "target nucleic acid sequence" in conjunction with a "distinguishing element") in the polynucleotide molecule. A "distinguishing element" is a nucleotide sequence in a polynucleotide molecule of interest capable of uniquely distinguishing the polynucleotide molecule of interest from other molecules that do not comprise the nucleotide sequence. The distinguishing element can be, for example, a polymorphism (such as a polymorphic oligonucleotide sequence, a single nucleotide polymorphism, a haplotype 'tag' single nucleotide polymorphism (tag SNP), a short tandem repeat), a deletion, an insertion, an inversion, a duplication, a translocation or another form of chromosomal rearrangement. The distinguishing element can also be, for example, a restriction site, a methylated restriction site, a methylated sequence motif, a protein binding site, a site, region or sequence found to be encoding SiRNA or targeted for silencing by SiRNA, or a sequence with a specific secondary structure.

In certain embodiments, the distinguishing element is allele-specific. As known in the art, "allele" refers to one of several alternative forms of a gene occupying a given locus on a chromosome. "Allele-specific" refers to a specific sequence capable of distinguishing a particular allele from the other alternative alleles. "Allele-specific extraction" refers to isolation of a polynucleotide molecule of interest based on an allele-specific sequence in the polynucleotide molecule. In certain embodiments, the distinguishing element is haplotype-specific. Also as known in the art, "haplotype" refers to a set of alleles or markers of closely linked genes that are usually inherited together.

"Haplotype-specific" refers to a specific sequence capable of distinguishing between different haplotypes of a gene, for example between a copy of the gene of maternal origin from that of a paternal origin at a heterozygous site. "Haplotype-specific extraction" refers to the isolation of a polynucleotide molecule of interest based on a haplotype-specific sequence in the polynucleotide molecule.

In certain other embodiments, the distinguishing element is locus-specific. As known in the art, "locus" refers to a position on a chromosome at which the gene for a particular trait resides. A locus may be occupied by any one of the alleles for the gene. "Locus-specific" refers to a specific sequence capable of distinguishing a particular locus from another locus. In general, the locus-specific sequence is a sequence shared by substantially all of the alleles (i.e., more than about 80% of all the alleles) occupying the locus, but different from sequences at another locus. In certain embodiments, a locus-specific sequence is a sequence shared by more than about 90%, 95%, or 98% of all the allele occupying a locus of interest. "Locus-specific extraction" refers to isolation of a polynucleotide molecule based on a locus-specific sequence in the polynucleotide molecule.

In certain embodiments, the distinguishing element is capable of distinguishing a polynucleotide molecule of interest from another nucleic acid molecule that is nearly identical to the polynucleotide molecule. A nucleic acid molecule is "nearly identical" to a polynucleotide molecule if they share over 95% sequence identity. In certain embodiments, the distinguishing element is capable of distinguishing a polynucleotide molecule of interest from another nucleic acid molecule that is more than 96%, 97%, or 99% identical to the polynucleotide.

In addition to a distinguishing element, a strand of a polynucleotide of interest also comprises a target nucleic acid sequence to which a targeting element is able to bind. In certain embodiments, the distance between the target nucleic acid sequence and the distinguishing element is between 100 nucleotides and 0 nucleotide (including any integer value between 100 and 0, such as 50, 20, 25, 10, 8, 7, 6, 5, 4, 3, 2, and 1). In different embodiments, the distinguishing element can be part of the target nucleic acid sequence, and preferably be located at or near the 5' terminus of the target nucleic acid sequence. The distance between a target nucleic acid sequence is calculated based on (1) the number of nucleotides between the 5' terminus of the target nucleic acid sequence and the 3' terminus of the distinguishing element if the target nucleic acid sequence is located 3' to the distinguishing element, and (2) the number of nucleotides between the 3' terminus of the target nucleic acid sequence and the 5' terminus of the distinguishing element if the target nucleic acid sequence is located 5' to the distinguishing element, except that in the embodiments where the distinguishing element is part of the target nucleic acid sequence, the distance between the distinguishing element and the target nucleic acid sequence is regarded as 0 nucleotide.

The terms "3'" and "5'" are used herein to describe the location of a particular site within a single strand of a nucleic acid molecule. When a location in a nucleic acid molecule is "3' to" or "3' of" a reference nucleotide or a reference nucleotide sequence, this means that the location is between the 3' terminus of the reference nucleotide or the reference nucleotide sequence and the 3' hydroxyl of that strand of the nucleic acid. Likewise, when a location in a nucleic acid is "5' to" or "5' of" a reference nucleotide or a reference nucleotide sequence, this means that it is between the 5' terminus of the reference nucleotide or the reference nucleotide sequence and the 5' phosphate of that strand of the nucleic acid molecule. Further, when a nucleotide sequence is "directly 3' to" (also used interchangeably with "immediately 3' to") or "directly 3' of" (also used interchangeably with "immediately 3' of") a reference nucleotide or a reference nucleotide sequence, this means that the 5' terminus of the nucleotide sequence is immediately next to the reference nucleotide or the 3' terminus of the reference nucleotide sequence. Similarly, when a nucleotide sequence is "directly 5' to" (also used interchangeably with "immediately 5' to") or "directly 5' of" (also used interchangeably with "immediately 5' of") a reference nucleotide or a reference nucleotide sequence, this means that the 3' terminus of the nucleotide sequence is immediately next to the reference nucleotide or the 5' terminus of the reference nucleotide sequence.

In certain embodiments, a target nucleic acid sequence is located 3' to a distinguishing element in one strand of a polynucleotide molecule of interest. In certain embodiments, a target nucleic acid sequence is located immediately 3' to a distinguishing element in one strand of a polynucleotide molecule of interest.

To isolate a polynucleotide molecule of interest from a nucleic acid population, a targeting element is used to bind to a target nucleic acid sequence in the polynucleotide molecule. A "targeting element" (also referred to as a "sequence-specific extraction probe" or "sequence-specific probe") refers to a molecule that binds specifically to a target nucleic acid sequence of a polynucleotide molecule of interest in a population of nucleic acid molecules. A molecule that "binds specifically to" a target nucleic acid sequence if under certain given conditions (e.g., in a nucleic acid extension reaction mixture), the molecule binds to a polynucleotide molecule that comprises the target nucleic acid sequence, but does not bind to nucleic acid molecules that do not comprise the target nucleic acid sequence.

In some embodiments, the targeting element is a nucleic acid, or a nucleic acid derivative that hybridizes to a complementary target nucleic acid sequence in a polynucleotide molecule of interest. Examples of nucleic acid-based nucleic acid derivatives include, e.g., an oligonucleotide, an oligopeptide nucleic acid (PNA), an oligo-LNA, or a ribozyme. The targeting element can alternatively be a polypeptide or polypeptide complex that binds specifically to a target nucleic acid sequence. Examples of polypeptide-based targeting elements include, e.g., restriction enzymes, transcription factors, RecA, nucleases, and other sequence-specific DNA-binding proteins. The targeting element can alternatively be a hybrid, complex or tethered combination of one or more of individual targeting elements.

The binding of a targeting element to a target nucleic acid sequence can occur as part of a discrete chemical or physical association. For example, association can occur as part of an enzymatic reaction, a chemical reaction, physical association, polymerization, ligation, restriction cutting, cleavage, hybridization, recombination, crosslinking, or a pH-based cleavage.

In certain embodiments, the targeting element is an oligonucleotide that is at least substantially complementary to a target nucleic acid sequence in a polynucleotide molecule of interest. An oligonucleotide is "at least substantially complementary to" a target nucleic acid sequence when the oligonucleotide is able to anneal to the target nucleic acid sequence in a given reaction mixture (e.g., a nucleic acid extension mixture). In certain embodiments, the targeting element is exactly or completely complementary to the target nucleic acid sequence, that is, each nucleotide of the targeting element is complementary to the nucleotide of the target nucleic acid sequence at its corresponding position.

In certain embodiments, a target nucleic acid sequence is immediately 3' to a distinguishing element in one strand of a polynucleotide molecule of interest, and a targeting element binds to the target nucleic acid sequence in that strand of the polynucleotide molecule so that the 3' terminal nucleotide of the targeting element binds to the 5' terminal nucleotide of the target nucleic acid sequence. As described in more detailed below, extension of the oligonucleotide in the presence of a terminating and immobilizable nucleotide complementary to a nucleotide in the distinguishing element allows for distinction between the polynucleotide molecule of interest and other nucleic acid molecules that do not contain the distinguishing element.

In certain embodiments, a target nucleic acid sequence is immediately 3' to a distinguishing element in one strand of a polynucleotide molecule of interest, and a targeting element binds to both the target nucleic acid sequence and the distinguishing element (or at least a portion of the distinguishing element) in that strand of the polynucleotide molecule so that the 3' terminal nucleotide of the targeting element binds to a nucleotide in the distinguishing element of the target nucleic acid sequence. Also as described in detail below, selective extension of the oligonucleotide using the strand of the polynucleotide molecule that comprises both the target nucleic acid sequence and the distinguishing element allows for distinction between the polynucleotide molecule of interest and other nucleic acid molecules that do not contain the distinguishing element.

The following provides detailed description of binding of an exemplary targeting element (i.e., an oligonucleotide) to a target nucleic acid sequence of a polynucleotide molecule of interest.

The targeting of a target nucleic acid sequence in a polynucleotide molecule with an oligonucleotide is straightforward when both are present in single-stranded form. A melting temperature can be calculated for each oligonucleotide-target nucleic acid sequence complex below which hybridization occurs. It is possible to adjust the hybridization conditions (mainly temperature and salt/cation concentration) such that only a perfectly matched oligonucleotide binds to the target nucleic acid sequence. Considerable literature and protocols exist on the polymerase chain reaction (PCR), dyeterminator sequencing reactions as well as mini-sequencing or primer extension reactions, which are of similar nature as the enzymatic distinction reaction in this invention (Molecular Cloning: A Laboratory Manual. Sambrook et al., Third Edition 2001, Cold Spring Harbor Laboratory Press, N.Y.; AmpliTaq™ product sheet, Perkin Elmer/Roche, Branchburg, N.J., and references therein). Single stranded DNA can be generated in several ways, for instance, by heating and subsequent quenching on ice, NaOH denaturation or physical separation based on biotinylated PCR-primers that get incorporated into only one copy of a PCR product (Molecular Cloning: A Laboratory Manual. Sambrook et al., Third Edition 2001, Cold Spring Harbor Laboratory Press, N.Y.; Mitchell and Merril, Anal Biochem. 1989 May 1; 178 (2):23942)

If the polynucleotide molecule of interest is present in a nucleic acid population as a double-stranded nucleic acid, such as genomic or plasmid DNA, the target nucleic acid sequence in the polynucleotide molecule of interest has to be rendered accessible in order for the oligonucleotide to bind to the sequence. This can be accomplished by thermal denaturation, that is, heating the sample to a temperature (e.g., higher than 65° C., 80° C. or 95° C.) at which the DNA begins to melt and form loops of single-stranded DNA. Thermal denaturation can be substituted by other methods that facilitate the binding of the targeting element to the target nucleic acid sequence, such as chemical denaturation (e.g., by alkaline incubation of polynucleotide molecules) or enzymatic strand separation (e.g., using helicase, RecA, etc.).

Under annealing conditions and typically in an excess of oligonucleotide relative to the polynucleotide molecule of interest, the oligonucleotides will, due to mass action as well as their usually smaller size and thus higher diffusion coefficient, bind to homologous regions before renaturation of the melted fragment strands occurs. Oligonucleotides are also able to enter double-stranded fragments at homologous locations under physiological conditions (37° C.) (Iyer et al., J Biol Chem. 1995 Jun. 16, 270(24):14712-7 and references cited therein).

This is relevant since the possibility of cross-hybridization between opposite strands of different alleles can lead to the extraction of a mismatched double-stranded hybrid of two alleles. It is usually undesirable to generate fully single-stranded template DNA due to this reason, although the likelihood for cross-hybridization to occur in a sample of genomic DNA is small. A robust link of the separation group and the distinguishing element, as discussed below, is able to retain the polynucleotide molecule that comprises the distinguishing element even under harsh denaturation and washing conditions.

Methods and kits have been developed to facilitate the sequence-specific introduction of oligonucleotides into double-stranded targets such as genomic or plasmid DNA and may be used in connection with the present invention (Iyer et al., J Biol Chem. 270(24):14712-7, 1995) and references cited therein; Teintze et al., Biochem Biophys Res Commun. 211(3):804-11, 1995; Honigberg et al., Proc Natl Acad Sci USA. 83(24):9586-90, 1986; Rigas et al., Proc Natl Acad Sci USA. 83(24):9591-5, 1986; Hakvoort et al., Nucleic Acids Res. 24(17):3478-80, 1996; Hakvoort et al., Gene Cloning and Analysis by RT-PCR, Edited by Siebert and Larrick, Biotechniques Books 1998, Natick, Mass.; ClonCapture™ cDNA Selection Kit, Clontech, Palo Alto, Calif.; and Welcher et al., Nucleic Acids Res. 14(24):10027-44, 1986). A coating of oligonucleotides with DNA-binding proteins such RecA (e.g., *E. coli* recombination protein "A") or staphylococcal nuclease speeds up their incorporation several orders of magnitude compared to the introduction of analogous unmodified oligonucleotides at higher concentration and significantly increases the stability of such complexes (Cunningham et al., Cell 24(1):213-23, 1981; Belotserkovskii et al., Biochemistry. 38(33):10785-92, 1999; and Sena and Zarling, Nat Genet. 3(4):365-72, 1993), while still permitting enzymatic elongation of the introduced oligonucleotide (Iyer et al., J Biol Chem. 270(24):14712-7, 1995 and references cited therein). In certain embodiments, polymerases with a strand displacement activity (e.g., Phi29 DNA polymerase and Obeta replicase) and 3'-exonuclease protected targeting elements may be used. For example, due to its strand displacement activity, Phi29 DNA polymerase may extend oligonucleotides or polynucleotides using a largely or completely double-stranded (i.e., not denatured) DNA as a template. The ability of Phi29 DNA polymerase to use non-denatured DNA as a template prevents breakage of template DNA during denaturation. However, because Phi29 DNA polymerase also has a proof-reading activity (i.e., an activity that corrects mismatched 3'-end of primers and then extend them), 3'-exonuclease protected primers (by using phosphorothioate bonds between the bases or by the incorporation of LNAs) are preferably used. Otherwise, the elimination of the mismatched 3'-end of primers would interfere with distinction among different polynucleotide molecules as discussed in detailed below.

Alternatively, or in addition, helper oligonucleotides may be used to facilitate opening of double-stranded regions and/or secondary structures of polynucleotide molecules. Such helper oligonucleotides are 3'-phosphorylated and thus will not be extended if added to a sequence-specific extraction reaction. However, they can function to help hybridization and facilitate opening of secondary structures in polynucleotide molecules. Description of helper oligonucleotides useful in the present invention may be found in U.S. Pat. Nos. 6,482,592; 5,387,510; 5,547,843; and 5,731,153.

All of the methods described above (as well as other known methods) that facilitate the sequence-specific introduction of oligonucleotides into double-stranded polynucleotide molecules of interest may be particularly useful where the extraction of relatively long polynucleotide molecules is desirable. Such methods reduce the use of denaturation steps, which may cause fragmentation of polynucleotide molecules of interest.

3. Distinction

In certain embodiments, the distinction between a polynucleotide molecule of interest and other nucleic acid molecules in a nucleic acid population is accomplished by selectively attaching an immobilizable separation group to a targeting element that binds to a target nucleic acid sequence in the polynucleotide molecule of interest. An immobilizable separation group is "selectively attached" to a targeting element if the immobilizable separation group is only attached to a targeting element that is bound to a target nucleic acid sequence in a polynucleotide molecule of interest that contains the distinguishing element, but not to any targeting element that is not bound to a target nucleic acid sequence in the polynucleotide molecule of interest (e.g., any targeting element that is not bound to any nucleic acid molecules, or any targeting element that is bound to a nucleic acid molecule other than the polynucleotide molecule of interest). Put differently, the selective attachment of an immobilizable separation group to a targeting element depends on whether or not the nucleic acid molecule to which the targeting element is bound is a polynucleotide molecule of interest (i.e., a nucleic acid molecule comprising a particular distinguishing element in the strand where a target nucleic acid sequence to which the targeting element binds is located).

In certain embodiments, the targeting element is an oligonucleotide and the target nucleic acid sequence is immediately 3' to the distinguishing element in one strand of the polynucleotide molecule of interest. In such embodiments, once the oligonucleotide binds to the targeting nucleic acid sequence in the polynucleotide molecule, it is enzymatically elongated in a 5' to 3' direction under appropriate conditions (e.g., in a nucleic acid extension reaction mixture). The elongation takes place by incorporation of individual nucleotides, whereby the identity of the base immediately adjacent to the 3'-terminus of the oligonucleotide (complementary to a nucleotide of the distinguishing element (e.g., a polymorphic site) establishes a differential in the elongated sequence. This differential can be exploited such that a unique modified nucleotide is provided containing a covalently linked separation element, such as biotin.

For example, if "A" is provided with a biotin moiety attached to it, only the extension product of the oligonucleotide bound to a polynucleotide molecule having a "T" at the polymorphic site will have a biotinylated "A". The oligonucleotides bound to other nucleic acid molecule will also get extended but the first extended nucleotide will not be biotinylated "A".

It is preferable that extension products of oligonucleotides bound to nucleic acid molecules other than the polynucleotide molecule of interest do not obtain a separation group. The incorporation of separation group into extension products of oligonucleotides that do not bind to the polynucleotide molecule of interest could, for instance, take place if further downstream to the polymorphic site, i.e., in the direction of enzymatic elongation, a nucleic acid molecule to which the oligonucleotide binds possess a "T", in which case a biotinylated "A" may be incorporated. The problem may be eliminated by use of terminating nucleotides, such that the elongation of the oligonucleotide stops after the first incorporated nucleotide and no separation group can be attached unless the base immediately adjacent to the 3'-end of the oligonucleotide leads to its incorporation.

A modification of the above method allows the use of non-terminating nucleotides. In this case, an oligonucleotide is chosen such that it anneals to not only the target nucleic acid sequence but also to the distinguishing element or at least a portion of the distinguishing element in a polynucleotide molecule of interest. Preferably, the 3' portion or 3' terminus of the oligonucleotide is complementary to (and anneals to) the distinguishing element or a portion thereof.

Conditions may be chosen so that the oligonucleotide gets elongated only if it anneals to the polynucleotide molecule of interest, but does not get elongated if it anneals to other nucleic acid molecules that do not contain the distinguishing element in the polynucleotide molecule of interest. The lack of the distinguishing element in the other nucleic acid molecules results in one or more mismatches (preferably at the 3' portion or 3' terminus of the oligonucleotide), which makes it difficult for a polymerase to extend the oligonucleotide. Such conditions include those that allows hybridization of a perfectly matched oligonucleotide to be highly favored over hybridization of the same oligonucleotide to any site containing a mismatch (Woolley et al., Nat Biotechnol. 18(7):7603, 2000) and those that prevents a polymerase from binding and initiating the polymerization if the oligonucleotide-nucleic acid complex contains a base-mismatch (Carver et al., Proc Natl Acad Sci USA. 91(22):10670-4, 1994). If biotinylated nucleotides are present in the reaction, they will only be incorporated into extension products of the oligonucleotides bound to the polynucleotide molecule of interest.

It is possible to use combinations of terminating and non-terminating nucleotides, and it is not in all cases necessary that the oligonucleotide binds immediately adjacent to the polymorphic site.

In this example an intervening sequence is present between the binding location of the targeting element and the polymorphic site distinguishing the two alleles:

```
5'-GATTACCAAAAATTC . . . 3'    (SEQ ID NO: 1)
                               (allele 1)

5'-GATTACCAAAAAGTC . . .       (SEQ ID NO: 2)
                               (allele 2)
```

The two alleles can be distinguished by use of an oligonucleotide that binds at the underlined sequence, in which case the heterozygous site, in bold script, is not immediately adjacent to the 3'-end of the oligonucleotide (the polymorphic site is a "T" in allele 1 and a "G" in allele 2) by, for instance, providing modified, but not necessarily terminating "A" with a separation group attached;

non-terminating "T" without a separation element;

unmodified, not necessarily terminating "G"; and terminating but otherwise unmodified "C"

When the reaction is carried out, only allele 1 will obtain a separation element by which it can be captured.

The selective attachment of separating groups to targeting elements (e.g., oligonucleotides) as described above may be performed by polymerase, such as DNA polymerases. In certain embodiments, the DNA polymerase is a processive DNA polymerase. "Processive DNA polymerases" refers to DNA polymerases that polymerize more than 100 nucleotides per polymerase-nucleic acid binding complex. In certain embodiments, processive DNA polymerases that polymerize more than 500, 1000, or 2000 nucleotides per polymerase-nucleic acid binding complex are used in the present application. Exemplary processive DNA polymerases include, but are not limited to, Phi29 DNA polymerase and Bca DNA polymerase.

In certain embodiments where selective attachment of separating groups to targeting elements (e.g., oligonucleotides) is performed by a DNA polymerase with a 3'→5' exonuclease activity (i.e., proofreading activity), it is recommended (although not absolutely necessary) that exonuclease resistant targeting elements be used.

It is possible to immobilize or otherwise capture very large molecules and complexes by a single separation group (Dapprich and Nicklaus, Bioimaging 6(1):25-32, 1998; Teintze et al., Biochem Biophys Res Commun. 211(3):804-11, 1995; Honigberg et al., Proc Natl Acad Sci USA. 83(24):9586-90, 1986; Rigas et al., Proc Natl Acad Sci USA. 83(24):9591-5, 1986; Hakvoort et al., Nucleic Acids Res. 24(17):3478-80, 1996; Hakvoort et al., Gene Cloning and Analysis by RT-PCR, Edited by Siebert and Larrick, Biotechniques Books 1998, Natick, Mass.; ClonCapture™ cDNA Selection Kit, Clontech, Palo Alto, Calif.; Welcher et al., Nucleic Acids Res. 14(24):10027-44, 1986; Hakvoort et al., Nucleic Acids Res., 24(17):347880, 1996; Tagle et al., Nature. 361(6414):751-3, 1993). If mere hybridization between homologous regions is utilized, the length of the oligonucleotide-separation group has to be chosen of sufficient size to prevent a loss of the fragment during manipulation. For fragments of several hundred to thousand bases size relatively short oligonucleotides (20 bases) are sufficient, whereas longer fragment molecules will require oligonucleotides that bind over larger distances. It is important to note in this context that under conditions of manipulating fragments relative to the surrounding solution by means of an oligonucleotide-separation group, the stability of hybridization is somewhat reduced, since temporary melting due to thermal fluctuations will occur on parts of the sequence that may lead to strand dissociation of a complex that is stable if there is no relative motion between components of the solution.

It is advantageous if a covalently or topologically linked bond is formed (or cleaved) between a separation element and a target nucleic acid sequence as a result of the reaction that distinguishes a polynucleotide molecule of interest and other nucleic acid molecules. This can be achieved by providing a reactive group linked to the separation group, so that upon selective incorporation of the separation group the reactive group is irreversibly attached to the target nucleic acid sequence only. Examples for reactions that can be used for this purpose are described for instance in Pfannschmidt et al., Nucleic Acids Res. 24(9):1702-9, 1996; Cimino et al., Annu Rev Biochem. 54:1151-93, 1985; Takasugi et al., Proc Natl Acad Sci USA. 88(13):5602-6, 1991; Zenkova et al., Eur J Biochem. 231 (3):726-35, 1995; Francois et al., Proc Natl Acad Sci USA.] 86(24):9702-6, 1989; Perrouault et al., Nature. 344(6264):358-60, 1990; Le Doan et al., Antisense Res Dev. 1(1):43-54, 1991; Barre et al., Proc Natl Acad Sci USA. 97(7):3084-8, 2000; Sun et al., Proc Natl Acad Sci USA. 86(23):9198-202, 1989; Sayers et al., Nucleic Acids Res 16(3):803-14, 19888; and Sayers et al., Nucleic Acids Res. 16(3):791-802, 1988. Examples for the formation of topologically linked bonds are described in Escude et al., Proc Natl Acad Sci USA. 96(19):10603-7, 1999; Antson et al., Nucleic Acids Res. 28(12):E58, 2000; and Nilsson et al., Nat Genet. 16(3):252-5, 1997.

Another method for selectively increasing the stability of the binding between the oligonucleotide-separation group complex and the polynucleotide molecule of interest is to provide a targeting element with the separation element already attached and further selectively stabilize the binding. The binding between an oligonucleotide-separation group complex and a polynucleotide molecule of interest is "selectively stabilized" if the binding between an oligonucleotide-separation group complex and a polynucleotide molecule of interest is stabilized while the binding between an oligonucleotide-separation group complex and nucleic acid molecules other than the polynucleotide molecule of interest is not stabilized or is stabilized to a less degree.

More specifically, in certain embodiments, an oligonucleotide may be first attached to one or more immobilizable separation groups (e.g., biotinylated nucleotides) and then annealed to both a target nucleic acid sequence and a distinguishing element (or a portion thereof) in a polynucleotide molecule of interest. The binding of the oligonucleotide and the polynucleotide molecule of interest may be stabilized by extending the 3' terminus of the oligonucleotide using the polynucleotide molecule as a template, either in the presence of regular nucleotides or in the presence of immobilizable nucleotides. The binding of the oligonucleotide and a nucleic acid molecule that does not comprise the distinguishing element, however, is not stabilized or is stabilized to a lesser degree due to the mismatch(es) (preferably at the 3' portion or 3' terminus of the oligonucleotide), which prevents efficient extension by a polymerase. In certain embodiments, the selective stabilization may be accomplished by ligation of the oligonucleotide with another nucleic acid fragment that is complementary to the region immediately 5' to the nucleotide to which the 3' terminus of the oligonucleotide anneals.

4. Separation

Separation groups useful in the present invention can be any moieties that facilitate subsequent isolation of attached targeting elements that are themselves associated with target nucleic acid sequence in polynucleotide molecules of interest. Such separation groups include those that can interact specifically with a cognate ligand. In certain embodiments, separation groups are immobilizable, which allows the separation of polynucleotide molecules associated with the separation groups via immobilization to an appropriate substrate. An exemplary separation group comprises or is an immobilizable nucleotide, e.g., a biotinylated nucleotide or oligonucleotide. Other examples of separation groups include ligands, receptors, antibodies, haptens, enzymes, chemical groups recognizable by antibodies or aptamers.

The separation group can be immobilized on any desired substrate. Examples of desired substrates include, but are not limited to, particles, beads, magnetic beads, optically trapped beads, microtiter plates, glass slides, papers, test strips, gels, spin columns, other matrices, nitrocellulose, and nylon. The substrate may comprise any binding partner capable of binding or cross-linking the separation group. For example, when the separation element is biotin, the substrate may comprise streptavidin, or variations such as neutravidin.

In certain embodiments, enzyme-driven incorporation is performed of a separation element, which becomes covalently attached to the targeting element (e.g., an oligonucleotide). For example, in certain embodiments, the targeting element is an oligonucleotide with an extendable 3' hydroxyl terminus and the separation group is an immobilizable nucleotide (such as a biotinylated nucleotide). The separation group may be attached to the targeting element by extending the oligonucleotide with a polymerase in the presence of the biotinylated nucleotide, thereby forming an extension product containing the immobilizable nucleotide. The targeting element can itself be covalently attached or topologically linked to the targeted polynucleotide (i.e., the polynucleotide molecule of interest), which allows washing steps to be performed at very high stringency and in turn results in reduced background and increased specificity.

In a final step, the reaction mixture is separated into a fraction that contains a polynucleotide molecule of interest (for example of maternal origin) and another fraction that contains other nucleic acid molecules (for example of paternal origin). This is accomplished by immobilizing to a solid support the polynucleotide molecule of interest of which the target nucleic acid sequence is bound to a targeting element-separation group complex. For instance, in the embodiments where a separation group comprises a biotinylated nucleotide, selective incorporation of the biotinylated nucleotide in an extension product of an oligonucleotide that anneals to a target nucleic acid sequence in a polynucleotide molecule of interest allows the polynucleotide molecule, but not other nucleic acid molecules, to be bound to streptavidin-coated magnetic beads. The beads may then be separated from the reaction mixture, allowing for separation of the polynucleotide molecule of interest bound to the beads from the remaining reaction mixture, which comprises other nucleic acid molecules.

As an optional step, the captured polynucleotide molecule of interest can then itself be separated from the beads (or another solid support) and eluted into a storage solution that does not contain any beads. This can be accomplished for example by heating the beads containing the bound polynucleotide molecule of interest in water to at least 70° C. for at least 1 second, or more typically to 80° C. for 10 minutes. The polynucleotide molecule of interest will separate and remain separated from the beads by reversible breakage of the biotin-streptavidin bond (see, Holmberg et al., *Electrophoresis* 2005, 26, 501-510). The magnetic beads are typically removed from a sample by drawing them to the side of a tube with a magnet or by centrifugation and aspirating the supernatant.

The advantage of removing the captured polynucleotide molecule of interest from the beads (or another solid support) is that some downstream amplification or typing assays may be sensitive to the presence of magnetic beads (or another solid support). For example at high concentrations, the beads may lead to interference with an optical or enzymatic step in an amplification or detection process. As described above, in certain embodiments where non-terminating immobilizable nucleotides are selectively incorporated into extension products of an oligonucleotide that is specifically bound to only a target nucleic acid sequence of a polynucleotide molecule of interest, a particularly strong attachment is formed by multiple binding events between multiple separation groups (e.g., biotinylated nucleotides) and solid support (e.g., streptavidin-coated beads). This is particularly advantageous for isolating a relative long polynucleotide molecule.

Due to the twisted helical structure of double-stranded DNA, extension products that comprise multiple separation groups (e.g., biotinylated nucleotides) can bind to a substrate (e.g., streptavidin-coated surface) in a way that topologically links the polynucleotide molecule of interest (which is annealed to the extension products) to the solid support, provided the distance of the extended region is significantly greater than the average distance between incorporated biotinylated nucleotides and the pitch of the helix (about 3.4 nm or ten basepairs per turn).

In a related version of the method, topologically improved binding of the polynucleotide molecule of interest to the solid support is achieved by the use of multiple targeting elements and separation groups that simultaneously bind the polynucleotide molecule to a solid support with intervening sequences in between each targeting element and separation group pair. It is necessary that such multiple targeting elements co-identify the polynucleotide molecule of interest so as to prevent binding of any of such elements to other nucleic acid molecules.

In certain embodiments, relatively large polynucleotide molecules of interest are isolated according to the present invention. Exemplary lengths of the relatively large polynucleotide molecules of interest extractable by the present invention include no less than about 5, 10, 15, 20, 25, 30, 40, 50, 60, 70, 80, 90, 100, 150, 200, 300, 400, 500, 600, 700, or 800 Kb, or no less than about 1 Mb.

In preparation for the separation step, it is advantageous to achieve fast on-rates as well as high selectivity and efficiency of binding between the polynucleotide molecule of interest and the solid support. If small polynucleotide molecules are to be separated, it is sufficient to carry out the binding step by incubation on a rotator at room temperature. In the case of large polynucleotide molecules, two factors will interfere with the reaction and result in slower and less efficient binding: a) a large polynucleotide molecule has a significantly reduced diffusion coefficient, and b) if only one separation element is associated with the polynucleotide molecule, other regions of the same molecule may interfere with the binding step by effectively shielding the separation element from getting into sufficiently close proximity to the solid support to initiate the binding reaction. Relative motion between the polynucleotide molecule with which a separation group is associated and the solid support overcomes both problems. This can be achieved by different means, for instance, by moving the beads used for capturing back and forth through the solution by magnetic action, by centrifugation, by repeated precipitation and resuspension, or by electrophoretically generated movement. It can alternatively be achieved by relative motion caused by the flow of the sample fluid through a fixed solid support, for example a porous membrane or matrix that contains immobilized streptavidin, for instance in a lateral flow device. The motion of the fluid through the support can be achieved by various means known in the art, for example by pumping, wicking, hydrophilic interaction, vacuum action, gravity flow, or centrifugation.

Any non-specific binding of nucleic acid molecules other than the polynucleotide molecule of interest to the solid support may result in incomplete separation of the polynucleotide molecule from other nucleic acid molecules. Especially single-stranded DNA may readily bind to untreated magnetic beads or other surfaces. The problem is overcome by exposing the surface to a solution containing components that saturate unspecific binding sites on the surface but do not interfere with the specific binding of the separation element (Duhamel and Whitehead, Methods Enzymol. 1990, 184:201-7). As an example, a blocking buffer "MBSB" may be used to suppress unspecific binding to beads (2.8 µm magnetic beads, Dynabeads M-280 Streptavidin, Dynal A. S., Oslo, Norway, or 1 µm polystyrene beads, Streptavidin Coated Latex, Interfacial Dynamics Corporation, Portland, Oreg.) with the result that biotinylated fragments are readily amplified by PCR while non-biotinylated fragments produced undetectable amplification products with both types of beads (magnetic or polystyrene).

Buffer "MBSA" is a solution containing 10 mM Tris pH 7.5, 2 mM EDTA, 0.2% Tween-20, 1 M NaCl, 5 µg/ml BSA, 1.25 mg/ml "carnation" dried milk (Nestle), 1 mg/ml glycine. Buffer "MBSB" is identical to "MBSB" with the addition of 200 ng/µl sheared salmon sperm DNA (GIBCO BRL), average size about 1000 basepairs, boiled for 3 min. and quenched on ice, and 50 nM each of oligonucleotides of the sequences TTAGTGCTGAACAAGTAGATCAGA (SEQ ID NO:3) and GTATATTCCAAGATCCATTAGCAG (SEQ ID NO:4).

Beads were washed twice in 1 ml "MBSA" by briefly vortexing and precipitating. Precipitation was performed with a particle collection magnet (Polysciences, Warrington, Pa.) for 1 min. (magnetic beads), or by centrifugation at 13,000 rpm on a table-top centrifuge for 3 min. (polystyrene beads). The beads were then incubated in 100 µl "MBSB" in a fresh tube rotating at RT for 2 hours and stored refrigerated in "MBSB".

Biotinylated and non-biotinylated fragments of identical sequence and 225 basepairs length were generated by PCR amplification of a region in the HLA (human leukocyte associated) locus.

An alternative to prevent contamination with non-specifically extracted nucleic acid molecule other than a polynucleotide of interest is to use a cleavable linker, which enables the selective release of targeted fragments into solution after separation has been completed (Dynal product sheet for Dynabeads M-280 Streptavidin, Dynal A. S., Oslo, Norway, www.dynal.no, and references cited therein, Pierce Chemical Technical Library: "Avidin-biotin", Pierce, Rockford, Ill., www.piercenet.com, and references cited therein; and Dawson et al., J Biol Chem. 264(22):12830-7, 1989).

In the embodiments where separation groups are attached to targeting elements before the targeting elements are contacted with a nucleic acid population and where the distinction between a polynucleotide molecule of interest and other nucleic acid molecules is accomplished by selective stabilization of the binding between the targeting element-separation complex and the polynucleotide molecule of interest, the immobilization of the polynucleotide molecule via the associated separation group should be performed under conditions so that only the selectively stabilized complexes that comprise the polynucleotide molecule of interest and the targeting element-separation group are immobilized to the substrate, but not complexes that comprise the targeting element-separation group and other, unstabilized nucleic acid molecules. Such conditions prevent or reduce the immobilized fraction from being contaminated with nucleic acid molecules other than the polynucleotide molecule of interest. Exemplary conditions include those that allow annealing between two relatively long nucleic acid fragments, but cause dissociation between a relatively short nucleic acid fragment from its annealing partner.

5. Multiplexing

If desired, the above-described methods can be repeated with a second targeting element by contacting the population of nucleic acid molecules with a second targeting element that binds specifically to a second target nucleic acid sequence in a second polynucleotide sequence of interest in the population of nucleic acid molecules. A second separation group is selectively attached to the second targeting element. The attached second separation group is then immobilized to a substrate, thereby forming a second immobilized targeting element-separation group complex to which the second polynucleotide molecule is bound. The immobilized targeting element-separation group complex to which the second polynucleotide molecule is bound is then removed from the population of nucleic acid molecules, thereby separating the second nucleic acid sequence of interest from the other nucleic acid molecules in the nucleic acid population.

In related embodiments, a second separation group is first attached to a second targeting element capable of specifically binding to a second target nucleic acid sequence of a second polynucleotide molecule of interest. The resulting second targeting element-separation group specifically binds to the second target nucleic acid sequence in the second polynucleotide molecule of interest. The binding between the second targeting element-separation group complex and the second polynucleotide molecule is then selectively stabilized. The stabilized complex that comprises the second targeting element-separation group complex and the second polynucleotide molecule is subsequently immobilized to a substrate under conditions that prevents the immobilization of unstabilized complex that comprises the second targeting element-separation group complex and nucleic acids other than the second polynucleotide molecule. The immobilized targeting element-separation group complex to which the second polynucleotide molecule is bound is then removed from the population of nucleic acid molecules, thereby separating the second nucleic acid sequence of interest from the other nucleic acid molecules in the nucleic acid population.

In certain embodiments, the steps and methods described above may be repeated multiple times sequentially. For example, a third targeting element and a third separation group may be used to isolate a third polynucleotide molecule of interest from the non-immobilized fraction that comprises nucleic acid molecules resulting from the isolation of the second polynucleotide molecule of interest. This process may be repeated a fourth, fifth, sixth, etc. time to isolate a fourth, fifth, sixth, etc. polynucleotide of interest.

In certain embodiments, the methods described above may be performed in a multiplexed fashion by targeting more than one (e.g., at least 3, 5, 10, 25, 50, 75, 100, 250, or 500) polynucleotides molecule of interest or more than one (e.g., at least 3, 5, 10, 25, 50, 75, 100, 250, or 500) regions of a polynucleotide molecule of interest at once.

In certain embodiments, the sequence-specific extraction performed in a multiplexed fashion (to extract multiple polynucleotide molecules of interest) according to the present invention comprises: (A) contacting a nucleic acid population that comprises multiple polynucleotide molecules of interest with multiple targeting elements so that each targeting element binds specifically to a target nucleic acid sequence of its corresponding polynucleotide molecule, wherein (i) each target nucleic acid sequence is located within 100 nucleotides of a distinguishing element in one strand of the polynucleotide molecule, and (ii) the distinguishing elements distinguish the polynucleotide molecules from other nucleic acid molecules that are nearly identical, (B) selectively attaching separation groups to the multiple targeting elements bound to the target nucleic acid sequences of corresponding polynucleotide molecules to form targeting element-separation group complexes, (C) immobilizing to substrate(s) via the separation groups the targeting element-separation group complexes to which the target nucleic acid sequences in the polynucleotide molecules are bound, and (D) removing the immobilized targeting element-separation group complexes to which the target nucleic acid sequences in the polynucleotide molecules are bound to isolate the polynucleotide molecules from the population of nucleic acid molecules.

In certain other embodiments, the sequence-specific extraction performed in a multiplexed fashion (to extract multiple polynucleotide molecules of interest) according to the present invention comprises: (A) contacting a nucleic acid population that comprises multiple polynucleotide molecules of interest with multiple targeting elements to which separation groups are attached so that each targeting element binds specifically to a target nucleic acid sequence of its corresponding polynucleotide molecule, wherein (i) each target nucleic acid sequence is located within 100 nucleotides of a distinguishing element in one strand of the polynucleotide molecule, and (ii) the distinguishing elements distinguish the polynucleotide molecules from other nucleic acid molecules that are nearly identical, (B) selectively stabilizing the polynucleotide molecules to form stabilized targeting element-separation group complexes to which the target nucleic acid sequences in the polynucleotide molecules are bound, (C) immobilizing to substrate(s) via the separation groups the targeting element-separation group complexes to which the target nucleic acid sequences in the polynucleotide molecules are bound, and (D) removing the immobilized targeting element-separation group complexes to which the target nucleic acid sequences in the polynucleotide molecules are bound to isolate the polynucleotide molecules from the population of nucleic acid molecules.

In certain embodiments, the sequence-specific extraction performed in a multiplexed fashion (to extract multiple regions in a single polynucleotide molecule of interest) according to the present invention comprises: (A) contacting a nucleic acid population that comprises a polynucleotide molecule of interest with multiple targeting elements so that each targeting element binds specifically to its corresponding target nucleic acid sequence in the polynucleotide molecule of interest, wherein (i) each target nucleic acid sequence is located within 100 nucleotides of its corresponding distinguishing element in one strand of the polynucleotide molecule, and (ii) each distinguishing element is capable of distinguishing the polynucleotide molecule from other nucleic acid molecules that are nearly identical, (B) selectively attaching a separation group to each of the multiple targeting elements bound to the target nucleic acid sequences of the polynucleotide molecule to form targeting element-separation group complexes, (C) immobilizing to a substrate via the separation group(s) the targeting element-separation group complexes to which the target nucleic acid sequences in the polynucleotide molecule are bound, and (D) removing the immobilized targeting element-separation group complexes to which the target nucleic acid sequences in the polynucleotide molecule are bound to isolate the polynucleotide molecule from the population of nucleic acid molecules.

In certain embodiments, the sequence-specific extraction performed in a multiplexed fashion (to extract multiple regions in a single polynucleotide molecule of interest) according to the present invention comprises: (A) contacting a nucleic acid population that comprises a polynucleotide molecule of interest with multiple targeting elements to each of which a separation group is attached so that each targeting element binds specifically to its corresponding target nucleic acid sequence in the polynucleotide molecule, wherein (i) each target nucleic acid sequence is located within 100 nucleotides of its corresponding distinguishing element in one strand of the polynucleotide molecule, and (ii) the distinguishing elements distinguish the polynucleotide molecules from other nucleic acid molecules that are nearly identical, (B) selectively stabilizing the binding of each targeting element to its corresponding target nucleic acid sequence in the polynucleotide molecule to form stabilized targeting element-separation group complexes to which the target nucleic acid sequences in the polynucleotide molecule is bound, (C) immobilizing to a substrate via the separation group(s) the targeting element-separation group complexes to which the targeting nucleic acid sequences in the polynucleotide molecule are bound, and (D) removing the immobilized targeting element-separation group complexes to which the target nucleic acid sequences in the polynucleotide molecule are bound to isolate the polynucleotide molecule from the population of nucleic acid molecules. As described above, multiplexed sequence-specific extraction may be accomplished by use of multiple oligonucleotides that specifically bind to different polymorphic sequences (i.e., different distinguishing elements) in a single polynucleotide molecule of interest or in multiple polynucleotide molecules of interest. If the polymorphisms are all of the same type (for instance all "T"s), all polynucleotide molecules of interest that comprise the polymorphisms can be extracted with the same type of separation group, for example, a biotinylated "A" (termed "first order multiplexing"). If the polymorphisms are of different types, various separation groups that comprise different immobilizable moieties attached to different types of nucleotides) can be used to selectively extract the corresponding polynucleotide molecules that comprise the polymorphisms (termed "second order multiplexing"). For instance, all polymorphisms of type "T" may be targeted by the use of a biotinylated "A" and extracted with streptavidin-coated beads, all polymorphisms of type "C" with fluorescein-modified "G" and beads containing antibodies against "G", and so on. This embodiment is especially useful if alleles of a sample are to be separated for which the genotype at a certain targeted polymorphic site is unknown. In certain embodiments where the polymorphisms are of different types, various separation groups (e.g., biotinalyted "A" and biotinalyted "G") that comprise same immobilizable moieties (e.g., a biotin) attached to different types of nucleotides (e.g., "A" and "G") can be used to selectively extract the corresponding polynucleotide molecules that comprise the polymorphisms. The use of same immobilizable moieties allows the immobilization of polynucleotide molecules of interest to be performed on a single type of substrates (e.g., streptavidin-coated beads) or a single substrate (a surface coated with a specific antibody).

In general, for multiplexed sequence-specific extraction to extract multiple regions in a single polynucleotide molecule of interest, the separation group(s) used are immobilizable to a same substrate. In certain embodiments, however, the separation group(s) used may be immobilizable to different substrates.

In one embodiment, a set of targeting elements for combined, multiplexed haplo-separation are designed to encompass a substantial portion of the genome or the whole genome and allow for potentially overlapping haplo-separations of any region, based on the polymorphisms found therein. In some embodiments, targeting elements are designed for preferred regions containing candidate genes located on multiple, typically unlinked loci. Depending on the preference of the user, multiplexed or sequential haplo-extractions may be targeting 1 to 1000 (including any integer value therebetween) or more unique sequence elements (i.e., distinguishing elements) at once. The initial targeting element set is typically small and increased as the need for additional genetic information is warranted. The captured polynucleotide molecules of interest may be as small as a few hundred basepairs, and are more typically about 50,000 to 100,000 bases in length if isolated from genomic DNA, and may extend to entire chromosomes if DNA isolation and haplo-separation protocols are used that preserve the integrity of the DNA starting material.

Figure 7A:
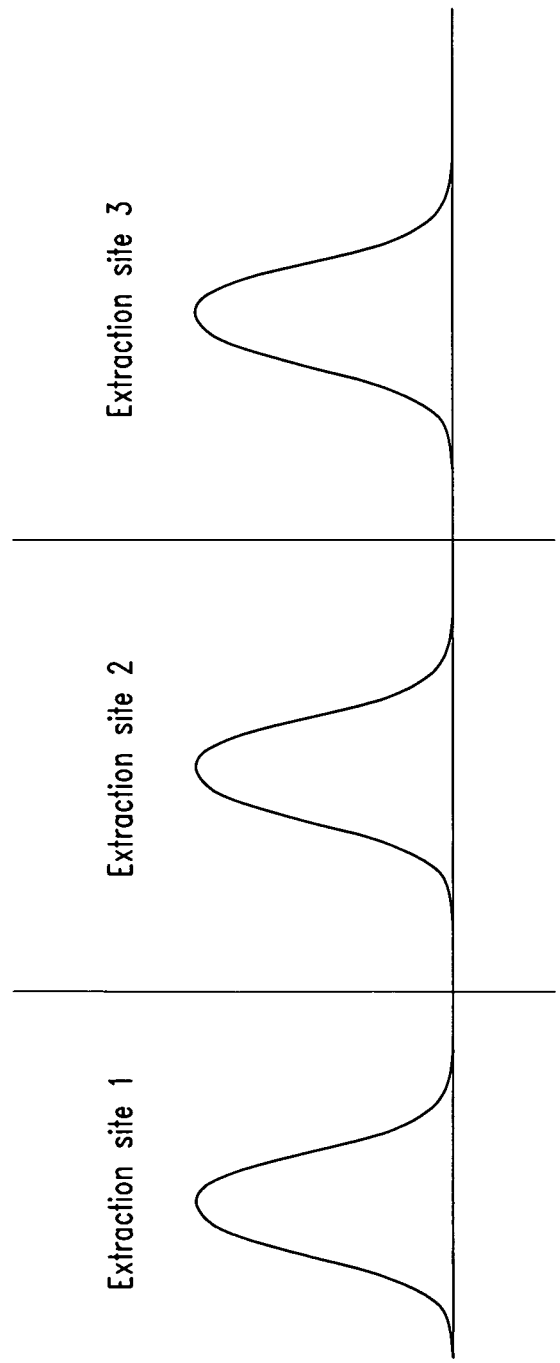
FIGS. 7A-7C are graphical representations showing interlaced multiplexing of sequence-specific extraction, which solves potential problem associated with physically overlapping polymorphic sites among different extraction products. For a single set of beads, multiplexed extraction sites are chosen so far apart that extracted fragments of extreme length still do not give rise to any detectable haplotype signal under certain given conditions (FIG. 7A). Multiple sets of beads (i.e., 3 sets—beads A, beads B, and beads C) may be used, but preferably each captured locus has been extracted by only one targeting element (also referred to as a "sequence-specific extraction probe") (FIG. 7B). Overlapping polymorphic sites are then typed for each batch of multiplexed beads and the contiguous haplotype is assembled based on the information from consecutive multiplexed extractions (FIG. 7C)

In certain embodiments where the present invention is used for haplotyping and where a single type of substrates (e.g., streptavidin-coated beads) or a single substrate is used, the locations of neighboring distinguishing elements on a region of a genome (also referred to as neighboring "extraction sites") should in general be sufficiently apart from each other so that no extracted polynucleotide molecules are longer than the distance between neighboring extraction sites (FIG. 7A). Otherwise, physically overlapping polymorphic sites may be present between polynucleotide molecules extracted from one extraction site and those extracted from a neighboring extraction site using a same substrate, which could give rise to spurious signals that might confound the true haplotype signal.

Figure 7B:
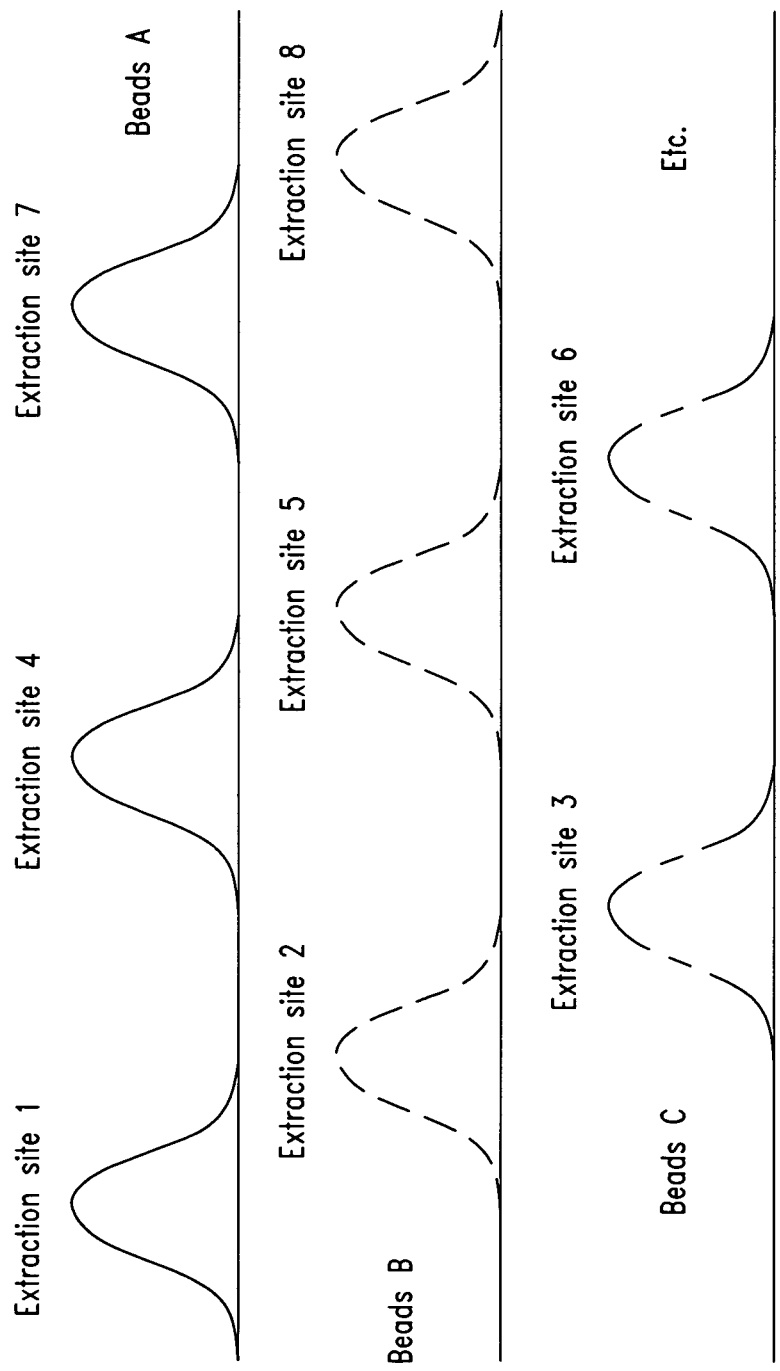

In certain embodiments where multiple types of substrates (e.g., streptavidin-coated beads and antibody-coated beads) are used for consecutive extractions to determine haplotype, similar to the above description, the neighboring extraction sites extractable using a single type of substrates (e.g., streptavidin-coated beads) should in general be sufficiently apart from each other so that no polynucleotide molecules extracted using that single type of substrates are longer than the distance between neighboring extraction sites. The above description is illustrated in FIG. 7B. More specifically, polynucleotide molecules isolated using beads A at Extraction Sites 1, 4, and 7 should not have overlap. Similarly, polynucleotide molecules isolated using beads B at Extraction Sites 2, 5, and 8 should not overlap, and polynucleotide molecules isolated using beads C at Extraction Sites 3 and 6 should not overlap.

Figure 7C:
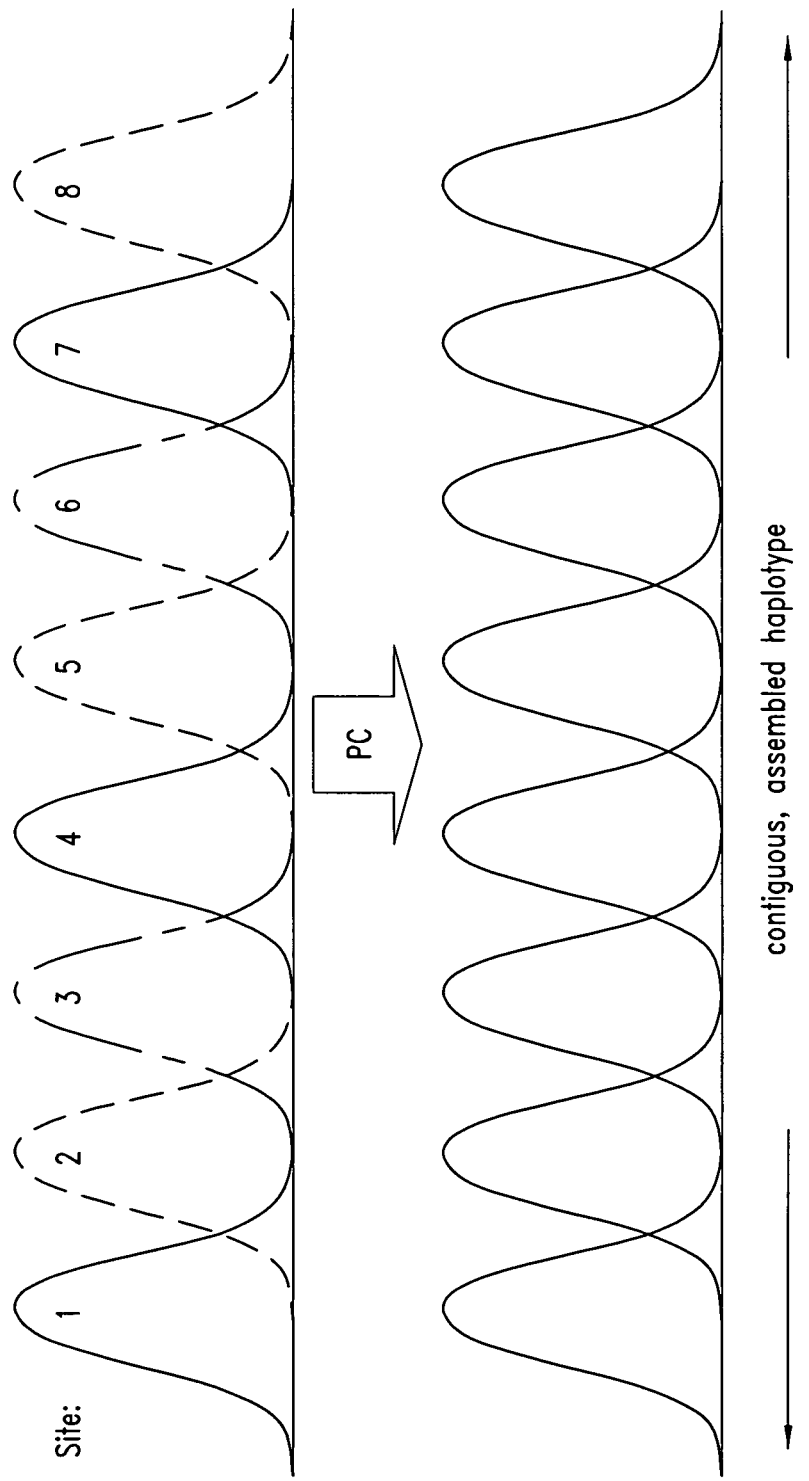

However, polynucleotide molecules extracted using one type of substrates (e.g., streptavidin-coated beads) may have overlapping polymorphic sites with polynucleotide molecules extracted using another type of substrates (e.g., antibody-coated beads). Such overlapping polymorphic sites are then typed for each batch of polynucleotide molecules extracted (i.e., polynucleotide molecules extracted using each type of substrates) and the contiguous haplotype is assembled based on the information from consecutive, multiplexed extractions. The above description is illustrated in FIG. 7C. More specifically, polynucleotide molecules isolated using beads A at Extraction site 1 may overlap with those isolated using beads B at Extraction site 2, polynucleotide molecules isolated using beads B at Extraction site 2 may overlap with those isolated using beads C at Extraction site 3, and so on. Polymorphic sites in polynucleotide molecules isolated using beads A, beads B and beads C are typed separately, and overlapping sites among polynucleotide molecules isolated using different beads (i.e., beads A, beads B, or beads C) are used to assemble a contiguous haplotype.

Accordingly, in one aspect, the present invention provides a method for assembling a haplotype comprising: (a) providing a nucleic acid population from an organism for which a haplotype is of interest; (b) separately isolating polynucleotide molecules by haplotype-specific extraction using multiple substrates, wherein (i) polynucleotide molecules are isolated at multiple extraction sites using each substrate, (ii) no polynucleotide molecules isolated at one extraction site using one substrate comprise a polymorphic site also present in polynucleotide molecules isolated at other extraction sites using the same substrate, (iii) one or more polynucleotide molecules isolated at one extraction site using one substrate comprise a polymorphic site also present in polynucleotide molecules isolated at a neighboring extraction site using other substrates, (c) separately characterizing polymorphic sites in polynucleotide molecules isolated using each substrate; (d) assembling a haplotype based on the characterization of polymorphic sites present in polynucleotide molecules isolated using more than one substrate. In certain embodiments, the method for assembling a hyplotype further comprises isothermally amplifying polynucleotide molecules isolated using the multiple substrates prior to step (c). However, isothermal amplification of isolated polynucleotide molecules are not always required prior to their characterization, and thus not used in certain other embodiments.

B. Nucleic Acid Amplification

The isolated polynucleotide molecules of interest as described above or portions thereof may be further isothermally amplified according to the present invention. Such amplification may be performed with the polynucleotide molecules of interest still attached to a substrate, or with the polynucleotide molecules of interest after dissociated from the substrate. The amplification may by generic, sequence-specific, or biased.

Figure 1B:
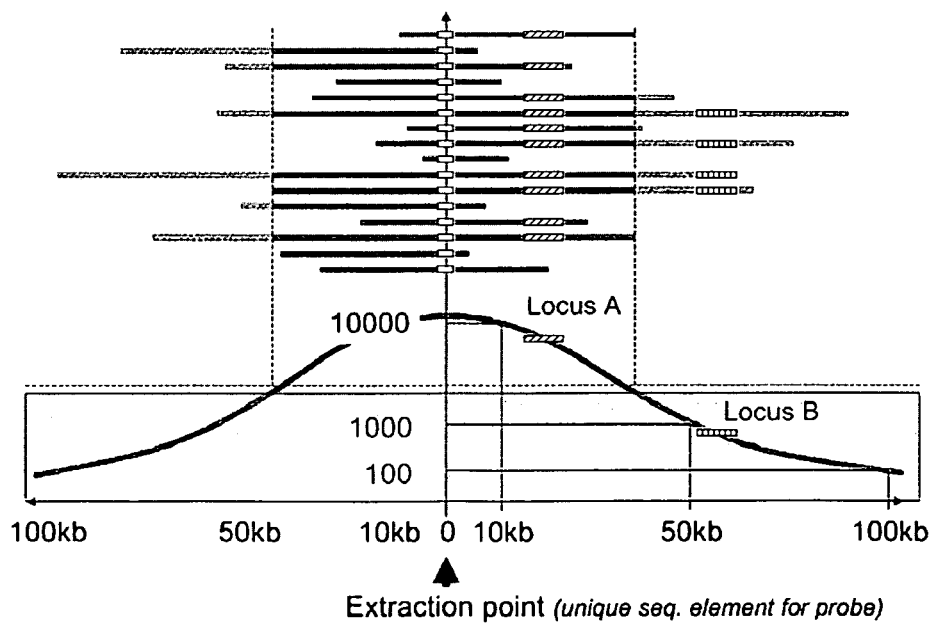
FIG. 1B is a graphical representation of the number of DNA molecules vs. length distribution for an isolated sample of nucleic acid molecules showing linkage between an Extraction Point and Locus A. The detection threshold and thus the directly achievable linkage distance are determined by the minimum number of template molecules that are required to obtain a detectable signal at a distant locus with a given assay.
Figure 1C:
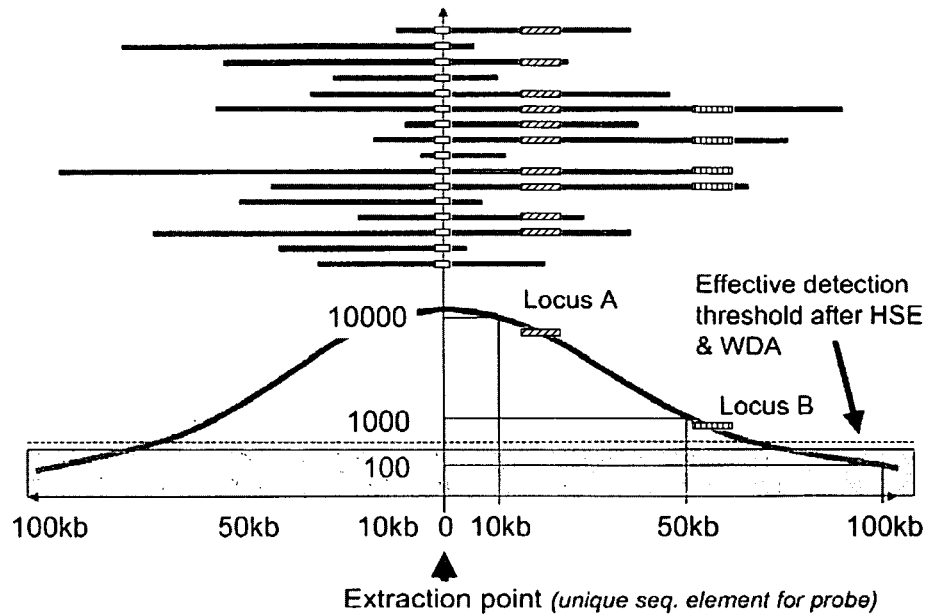
FIG. 1C is a graphical representation of the number of DNA molecules vs. length distribution for an isolated sample of nucleic acid molecules showing linkage between an Extraction Point, Locus A, and Locus B after an amplification of all captured material is performed. The overall template copy number has been increased and can lead to an effective lowering of the detection threshold and an increase in detectable linkage distance.

The amplification increases the number of nucleic acid molecules that comprise a locus of interest and thus enhances sensitivity of subsequent analysis (FIGS. 1A-1C). More specifically, FIG. 1A shows the number of DNA molecules and their length distribution of an isolated polynucleotide sample. The extraction point corresponds to the location of the distinguishing element used to isolate polynucleotide molecules from an initial nucleic acid population. FIG. 1B shows that linkage between an extraction point and Locus A. Because Locus A is located relatively close to the extraction point, the isolated polynucleotide sample contains a sufficient amount of polynucleotide molecules that comprise Locus A. The isolated polynucleotide sample may thus be directly used to detect and analyze Locus A. FIG. 1C shows that linkage among an extraction point, Locus A and Locus B. Unlike Locus A, Locus B is relatively distant from the extraction point. The isolated polynucleotide sample does not contain a sufficient amount of polynucleotide molecules that comprise Locus B in order for Locus B to be directly detected or analyzed. However, amplifying the polynucleotide sample according to the present invention increases the amount of polynucleotide molecules that comprise locus B and allows for subsequent detection and analysis of this locus.

1. Generic Amplification

Figure 2A:
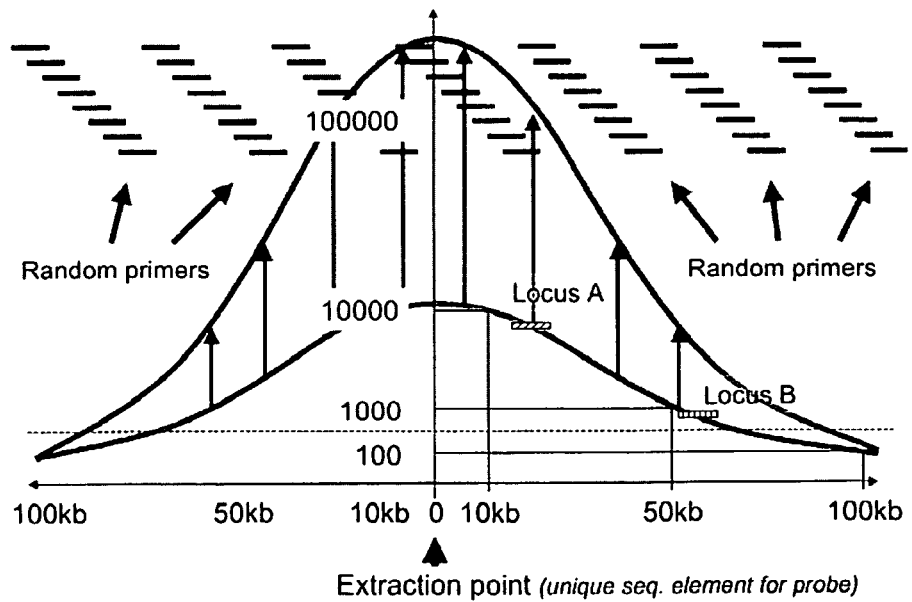
FIG. 2A is a graphical representation of the number of DNA molecules vs. length distribution following non-biased (generic) amplification of captured DNA.

"Generic amplification" refers to amplification of polynucleotide molecules wherein only random primers are used. Generic amplification is illustrated schematically in FIG. 2A. In certain embodiments, primers may be between 6 and 40 nucleotides in length, such as between 6 and 30, or between 8 and 20 nucleotides in length.

Generic amplification is also referred to as "whole DNA amplification" (WDA). In addition, if isolated polynucleotide molecules are genomic DNA, generic amplification is also referred to as "whole genome amplification" (WGA).

Generic amplification increases the number of template molecules that are available at any given locus. This reduces the threshold level at which a reliable signal can be detected and also increases the distance over which the linkage of multiple loci (shown as Locus A and Locus B in FIGS. 1B and 1C) can be definitively established.

Figure 5:
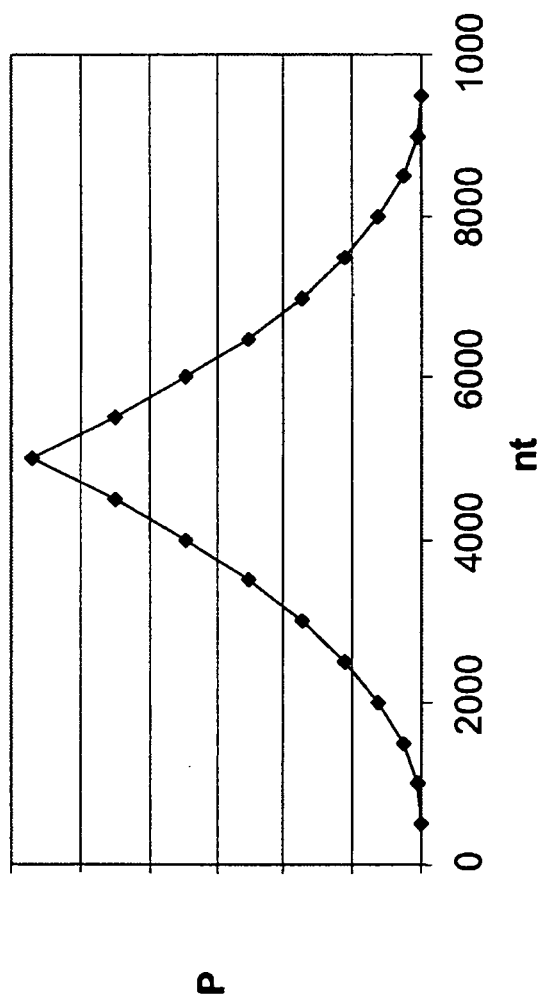
FIG. 5 shows a relative probability distribution (p) versus nucleotide position for the presence of amplified outer and inner regions of a 10 kb long fragment after multiple strand displacement amplification using random primers that bind approximately every 500 nucleotides. Inner regions are preferentially amplified compared to outer regions that are located near the 5'- or 3-'ends of the fragment.

Depending on reaction conditions, polynucleotide molecules to be amplified, and lengths of random primers, random primers generally bind approximately every 200 to 1000 nucleotides in each strand along the polynucleotide molecules. If strand displacement amplification is used in combination of random primers, the inner regions of template polynucleotide molecules would be amplified exponentially. In contrast, regions located near either terminus of the template polynucleotide molecules would be amplified substantially linearly. This results in a higher copy number of inner regions compared to regions at the end of the template polynucleotide molecules. This is shown in FIG. 5, where the probability (p) for the presence of outer and inner regions in a 10 kb long fragment after strand displacement amplification using random primer that bind approximately every 500 nucleotides is calculated.

2. Sequence-Specific Amplification

"Sequence-specific amplification" refers to amplification of a polynucleotide molecule wherein only sequence-specific primers are used. A primer is "specific to" a sequence of interest (e.g., a polynucleotide molecule isolated by sequence-specific extraction) if it anneals to the sequence of interest under certain given conditions, but does not anneal to other nucleic acid molecules in an amplification reaction mixture under the same conditions.

In certain embodiments, the sequence-specific amplification according to the present invention is locus-specific. "Locus-specific amplification" refers to amplification of a polynucleotide molecule wherein only primers specific to a particular locus are used. Each amplification product of a locus-specific amplification comprises at least a portion of the sequence of the locus of interest.

A primer is "specific to" a locus if under certain given conditions (e.g., under isothermal conditions for nucleic acid amplification), it binds to a common sequence within, or flanking, the locus shared by all or a majority of the alleles occupying the locus, but does not bind to other sequences (e.g., sequences of other loci). A sequence "flanks" a locus if the sequence is located outside the locus but the distance between the sequence and a nearby terminus of the locus is within 500 nucleotides. In certain embodiments, a sequence flanking a locus is 300, 200, 150, 100, 50 nucleotides apart from a nearby terminus of the locus.

In certain embodiments, locus-specific primers may be between 6 and 40 nucleotides in length, such as between 6 and 30, or between 8 and 20 nucleotides in length. In certain embodiments, more than 50% of the nucleotides (e.g., more than 70%, 80%, 85%, 90%, 95%, or 98%) in a locus-specific primer are complementary to their corresponding nucleotides in one strand of a template polynucleotide molecule.

In certain embodiments, the primers are designed so that 30% to 100% of regions of highest amplification rates overlap with a region of interest. In certain embodiments, about 50% to 100% or about 80% to 100% of regions of highest amplification rates overlap with a region of interest.

In certain embodiments, both sense and anti-sense primers are used. A "sense primer" is a primer that anneals to a portion of the strand of a polynucleotide molecule that comprises a target nucleic acid sequence and a distinguishing element. An "anti-sense primer" is a primer that anneals to the strand of a polynucleotide molecule that does not comprise a target nucleic acid sequence or a distinguishing element.

Figure 6A:
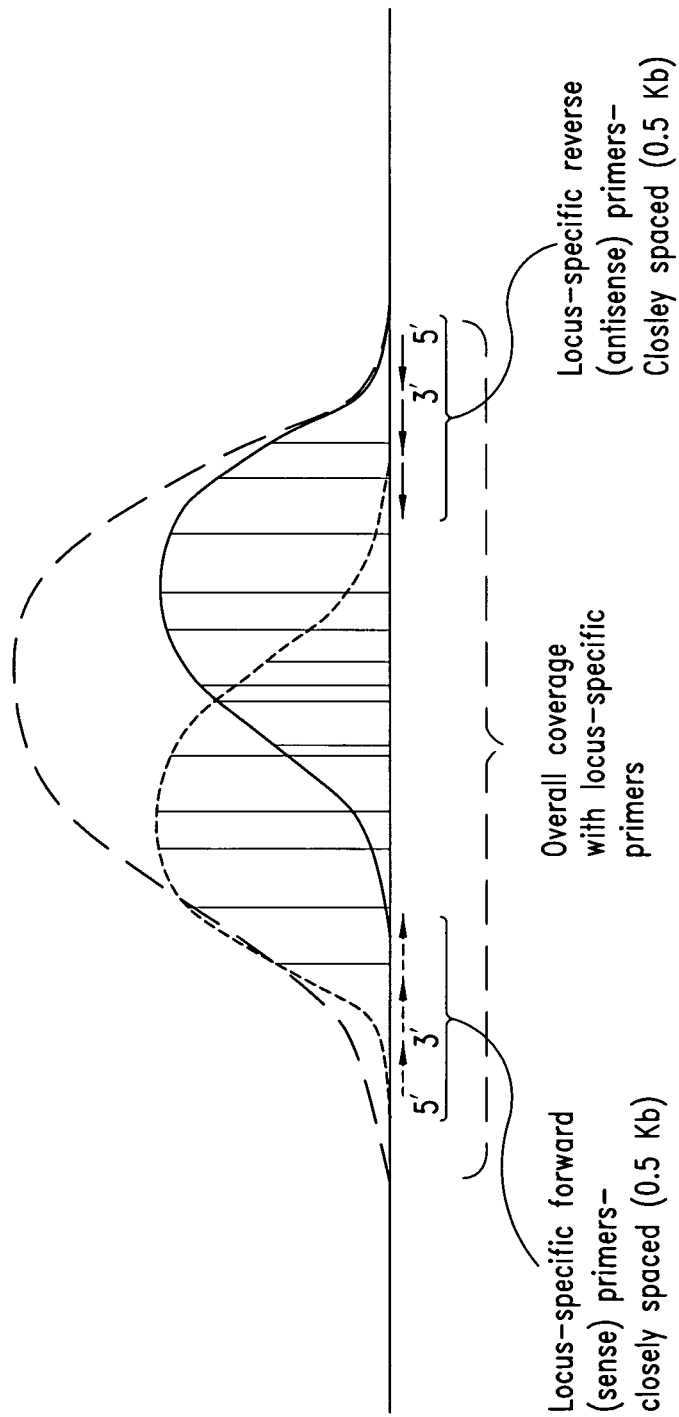
FIG. 6A shows amplification primers that are preferentially located near the ends of the target fragment and directional (5'→3') towards the center of the target fragment.
Figure 6B:
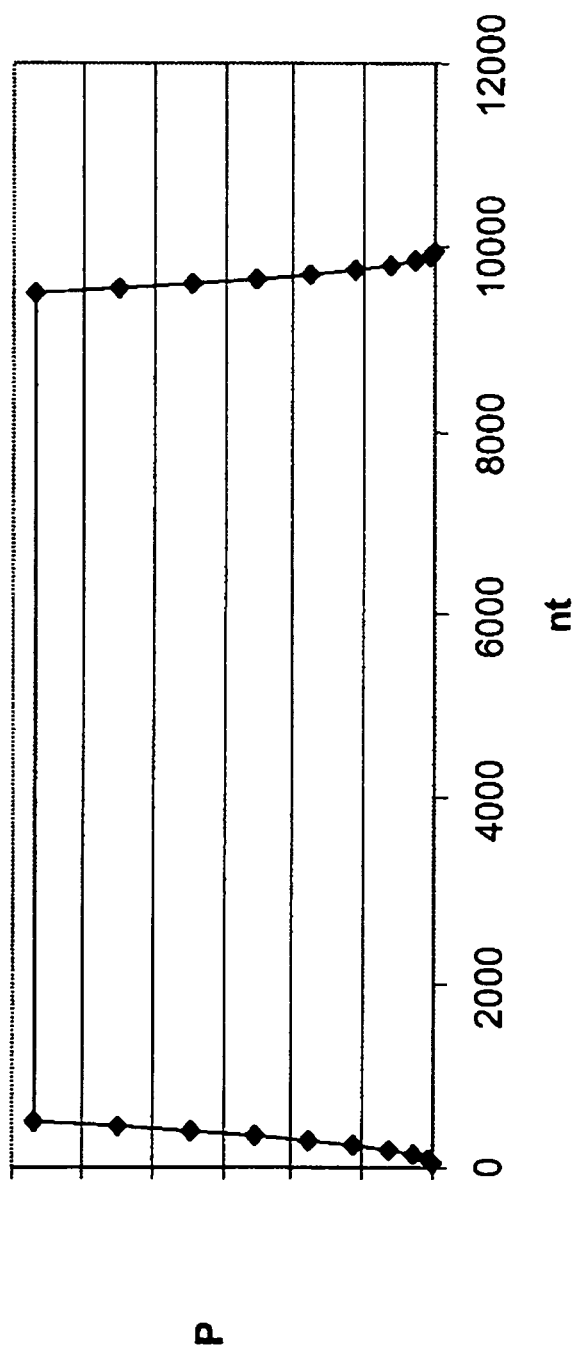
FIG. 6B shows a relative probability distribution (p) versus nucleotide position for the sequence representation of different regions of a 10 kb DNA fragment after multiple strand displacement amplification using 10 primers chosen to be specific to each terminus of the DNA fragment; with the distances between adjacent primers being 50 nucleotides.

In certain embodiments, multiple sequence-specific sense and anti-sense primers are used to increase the amplification rate and/or to ensure sufficient amplification of template polynucleotide molecules, especially near the two termini of the template polynucleotide molecules. In certain embodiments, more than 4, 6, 8, or 10 primers that anneal in close vicinity of each of the two termini of a template polynucleotide molecule are used. The closer the distance between the primers and the terminus of a template polynucleotide molecule near which the primers anneal, the higher the probability of highest amplification rate over the whole template polynucleotide molecule. In certain embodiments, the distances between the primers and the terminus of a template polynucleotide molecule near which the primers anneal are between 1 and 1000 nucleotides, such as between 1 and 500 nucleotides or between 1 and 250 nucleotides. FIG. 6B shows relative probability of sequence representation of different regions of 10 Kb DNA fragment from nucleic acid amplification using 10 primers specific to each terminus of the DNA fragment with the distances between adjacent primers being 50 nucleotides.

In certain related embodiments, multiple sequence-specific sense and anti-sense primers are used to increase the amplification rate and/or to ensure sufficient amplification of a locus of interest, especially near the two termini of the locus. In certain embodiments, more than 4, 6, 8, or 10 primers that anneal in close vicinity of each of the two termini of a locus of interest are used. The closer the distance between the primers and the terminus of a locus of interest near which the primers anneal, the higher the probability of highest amplification rate over the whole locus. In certain embodiments, the distances between the primers and the terminus of a locus of interest near which the primers anneal are between 1 and 1000 nucleotides, such as between 1 and 500 nucleotides or between 1 and 250 nucleotides.

In certain embodiments, end-specific primers are used together with center-specific primers for amplifying polynucleotide molecules or regions thereof (e.g., via strand displacement). The addition of center-specific primers to a reaction with end-specific primers may be useful for amplifying long template polynucleotide molecules. In certain embodiments, the lengths of template polynucleotide molecules may be at least about 5, 10, 15, 20, 25, 30, 40, 50, 60, 70, 80, 90, 100, 150, 200, 300, 400, 500, 600, 700, or 800 Kb, or no less than about 1 Mb.

"End-specific primers" are (i) primers that anneal to a template polynucleotide molecule within 500 nucleotides from a neighboring end of the template polynucleotide if the whole polynucleotide molecule is intended to be amplified, or (ii) primers that anneal to a template polynucleotide molecule in a polynucleotide molecule located within 500 nucleotides from a neighboring end of a particular region of interest (e.g., a locus) if only the particular region of interest is intended to be amplified. In the former case, end-specific primers anneal to a location within the template polynucleotide molecule of interest. In the latter case, end-specific primers may anneal to a location within the particular region of interest, or may anneal to a location flanking the particular region of interest (i.e., outside the particular region of interest).

"Center-specific primers" are primers that anneal to a template polynucleotide molecule of interest more than 500 nucleotides apart from a neighboring end of the polynucleotide molecule if the whole polynucleotide molecule of interest is intended to be amplified, or (ii) primers that anneal to a particular region (e.g., a locus) of a template polynucleotide molecule located more than 500 nucleotides apart from a neighboring end of the particular region of interest if only the particular region of interest is intended to be amplified.

In certain embodiments, the distances between neighboring end-specific primers are between 1 to 500 nucleotides (e.g., between 10 and 400 nucleotides, between 20 and 300 nucleotides, between 30 and 200 nucleotides, between 40 and 100 nucleotides, between 50 and 80 nucleotides). In certain embodiments, the average distance between neighboring end-specific primers are between 50 and 250 nucleotides (including any values therebetween, such as about 100 nucleotides).

In certain embodiments, the distances between neighboring center-specific primer are between 1 and 10,000 nucleotides (e.g., between 10 and 5,000 nucleotides, between 50 and 2000 nucleotides, or between 100 and 1000 nucleotides). In certain embodiments, the average distance between neighboring center-specific primers are between 100 and 5000 nucleotides (including any values therebetween, such as about 2000 nucleotides).

Both end-specific primers and center-specific primers may be sense primers or antisense primers. In certain embodiments, both sense end-specific primers and anti-sense end-primers are present in an amplification reaction mixture. In certain embodiments, both sense center-specific primers and anti-sense center-specific primers are present in an amplification reaction mixture. In certain embodiments, sense end-specific primers, anti-sense end-specific primers, sense center-specific primers and anti-sense center-specific primers are present in an amplification reaction mixture.

In certain other embodiments, end-specific primers may be used in the absence of any center-specific primers. Such primers are designed to be directional (5'→3') towards the center of a template polynucleotide molecule or of a region of interest in a template polynucleotide molecule (FIG. 6A).

3. Sequence-Biased Amplification

"Sequence-biased amplification" is a hybrid of generic amplification and sequence-specific amplification. It is performed in the presence of both random primers and sequence-specific primers.

Figure 2B:
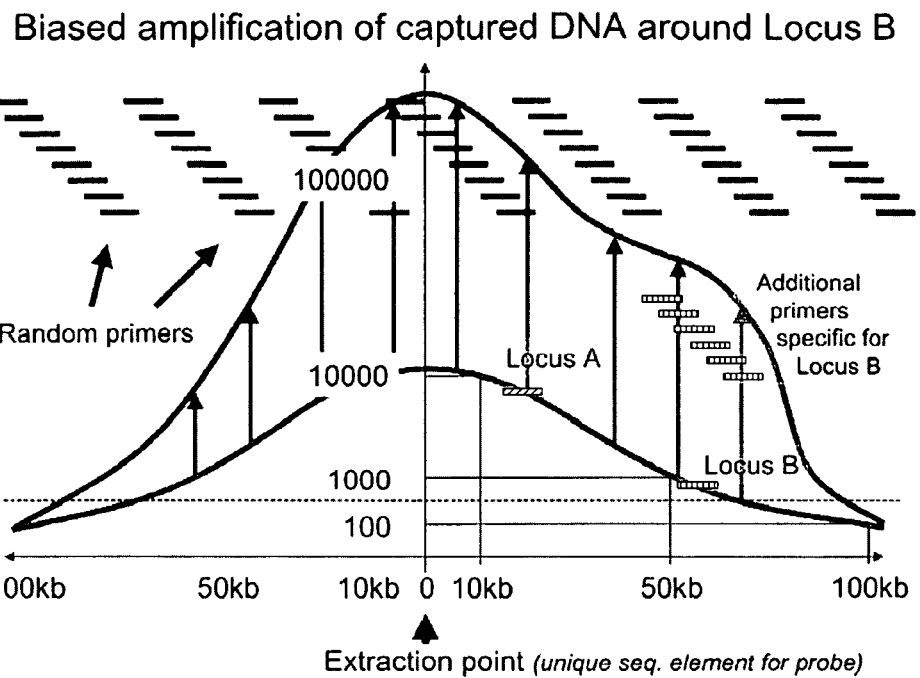
FIG. 2B is a graphical representation of the number of DNA molecules vs. length distribution following biased amplification (combination of generic and locus-specific amplification) of captured DNA.

In certain embodiments, sequence-biased amplification is locus-biased. "Locus-biased amplification" is a hybrid of generic amplification and locus-specific amplification. It is performed in the presence of both random primers and locus-specific primers (FIG. 2B). Locus-biased amplification results in preferentially amplification of the locus of interest relative to other polynucleotide molecule in an isolated nucleic acid sample. For example, if an extraction at HLA-B is performed and linkage to HLA-C is sought, it is advantageous to not only use random primers for WDA but to 'spike' the amplification mix with primers designed to bind in the region around the HLA-C locus. In this way, the locus-specific primers will preferentially amplify the specific region(s) (HLA-C in this example), but not in a strictly locus-specific way as during PCR.

The use of random primers in combination of sequence specific primers is useful, especially for the amplification of long template polynucleotide molecules or amplification of multiple regions in long template polynucleotide molecules. In certain embodiments, the lengths of template polynucleotide molecules may be at least 5, 10, 20, 40, 50, 60, 80, 100, 200, 400, or 500 Kb.

In certain embodiments, random primers are designed (e.g., with appropriate lengths) so that the distance between neighboring random primers are about 1 to 10 Kb (including any value therebetween). In certain embodiments, the average distance between neighboring random primers is about 2 Kb.

In certain embodiments, the distances between neighboring sequence-specific primers are between 2 and 10 Kb (including any value therebetween). In certain other embodiments, the distances between neighboring sequence-specific primers are between 0.1 to 0.9 Kb (including any value therebetween, such as about 0.5 Kb).

In certain embodiments, end-specific primers are used together with degenerate center-specific primers for amplifying polynucleotide molecules or regions thereof (e.g., via strand displacement). A "degenerate primers" is a sequence-specific primer whose sequence has several possible bases at certain positions. In certain embodiments, degenerate center-specific primers are a mixture of similar but not identical center-specific primers of the same sequence length and targeted to a same template polynucleotide position.

In certain embodiments, the distances between neighboring end-specific primers are between 1 to 500 nucleotides (e.g., between 10 and 400 nucleotides, between 20 and 300 nucleotides, between 30 and 200 nucleotides, between 40 and 100 nucleotides, between 50 and 80 nucleotides). In certain embodiments, the average distance between neighboring end-specific primers is between 50 and 250 nucleotides (including any values therebetween, such as about 100 nucleotides). In certain embodiments, the distances between neighboring degenerate center-specific primer are between 1 and 10,000 nucleotides (e.g., between 10 and 5,000 nucleotides, between 50 and 2000 nucleotides, or between 100 and 1000 nucleotides). In certain embodiments, the average distance between neighboring center-specific primers is between 100 and 5000 nucleotides (including any values therebetween, such as about 2000 nucleotides).

4. Amplification Procedures

As described above, the polynucleotide molecules isolated by sequence-specific extraction or a fragment thereof may be isothermally amplified according to the present invention. Isothermal amplification is especially useful in amplifying isolated large polynucleotide molecules (or fragments thereof) compared to those that require temperature cycling such as polymerase chain reaction (PCR) (see, e.g., Saiki et al., 1995. Science 230: 1350-1354), ligase chain reaction (see, e.g., Barany, 1991, Proc. Natl. Acad. Sci. USA 88: 189-193; Barringer et al., 1990, Gene 89: 117-122) and transcription-based amplification (see, e.g., Kwoh et al., 1989, Proc. Natl. Acad. Sci. USA 86: 1173-1177). For example, isothermal amplification circumvents the loss of sensitivity for amplifying large polynucleotide fragments associated with PCR-based amplification technologies, resulting from (1) ineffective thermal denaturation of a large fragment and (2) a low processivity of used polymerases.

"Isothermal amplification", "amplifying polynucleotide molecules isothermally" or the like refers to nucleic acid amplification performed under isothermal conditions. "Isothermal conditions" refers to amplification conditions under which amplification is performed at a given temperature or a narrow range of temperatures without thermal cycling. The reaction temperature can be of any temperature between 20° C. and 80° C. (e.g., between 25° C. and 75° C., and between 30° C. and 70° C.). The variation of temperatures under isothermal conditions (i.e., the difference between the maximum temperature and the minimum temperature) under which an isothermal nucleic acid amplification is performed should be less than 20° C. (e.g., less than 10° C., or less than 5° C.).

Exemplary isothermal amplification systems useful in the present invention include, but are not limited to, self-sustaining, sequence replication (see, e.g., Guatelli et al., Proc. Natl. Acad. Sci. USA 87: 1874-1878, 1990); the Qβ replicase system (see, e.g., Lizardi et al., BioTechnology 6: 1197-1202, 1988); strand displacement amplification (see, Nucleic Acids Res. 20(7):1691-6, 1992); the methods described in PNAS 89(1):392-6, 1992; NASBA (see, J Virol Methods. 35(3):273-86, 1991); rolling circle-based amplification (RCA) (see, e.g., U.S. Pat. Nos. 5,714,320 and 5,854,033; Hatch et al., Genet. Anal. Biomol. Engineer. 15:35-40, 1999; and Reagin et al., Journal of Biomolecular Techniques, 14:143-48, 2003).

In certain embodiments, isothermal nucleic acid amplification is performed using a strand displacement amplification method. "Strand-displacement" refers to a complete or partial conversion of a double-stranded nucleic acid molecule to a single-stranded nucleic acid molecule. Strand displacement may be facilitated by an activity of a polymerase (e.g., RecA, Phi29 DNA polymerase, Bca DNA polymerase, helicase, T4-gp32, etc.) or another enzyme. "Strand displacement amplification" refers to amplification resulting from primer extensions using a single-stranded portion of a double-stranded nucleic acid molecule as a template where strand displacement is employed to generate the single-stranded portion from the double-stranded nucleic acid molecule.

In general, isothermal amplification according to the present invention is specific to polynucleotide molecules isolated by sequence-specific extraction. In other words, such amplification amplifies polynucleotide molecules isolated by sequence-specific extraction, without any significant contamination of other nucleic acid molecules. "Without any significant contamination" refers to the fraction of nucleic acid molecules other than polynucleotide molecules isolated by sequence-specific extraction or their amplification products is less than 50%. In certain embodiments, the fraction of nucleic acid molecules other than polynucleotide molecules isolated by sequence-specific extraction or their amplification products is less than 25%, 15%, 10% or 5%.

5. Primers

Primers for amplification are typically oligonucleotides of sufficient length and appropriate sequence so as to provide the desired generic or locus-specific amplification. Specifically, the term "primer" as used herein refers to a sequence comprising six or more deoxyribonucleotides or ribonucleotides, which sequence is capable of initiating synthesis of a primer extension product and substantially complementary to a nucleotide sequence of interest. Environmental conditions conducive to synthesis include the presence of nucleoside triphosphates and an agent for polymerization, such as DNA polymerase, and a suitable temperature and pH. The primer is preferably single-stranded for maximum efficiency in amplification, but may be double stranded. If double-stranded, the primer is first treated to separate its strands before being used to prepare extension products. In certain embodiments, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers are generally designed to be substantially complementary to each strand of the genomic locus to be amplified and include the appropriate G or C nucleotides as discussed above. This means that the primers must be sufficiently complementary to hybridize with their respective strands under conditions that allow the agent for polymerization to perform. In addition, primers useful for nucleic acid amplification according to the present application are designed in a direction (i.e., 5'→3') so that the extensions from their 3'-termini produce products that comprise at least a portion of template sequences (or complement thereof) intended to be amplified.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage et al., Tetrahedron Letters, 22:1859-1862, 1981. An exemplary method for synthesizing oligonucleotides on a modified solid support is described in U.S. Pat. No. 4,458,066.

In certain embodiments, RecA-coated primers may be used to facilitate strand invasion of a double-stranded template polynucleotide molecule without requiring denaturation.

In certain other embodiments, 3'-exonuclease protected primer may be used. In conjunction with Phi29 DNA polymerase, such primers allow for continuous amplification even across double-stranded regions of a template polynucleotide molecule.

6. Polymerases

In general, any polymerase capable of extending a primed 3'-OH group activity may be used in amplifying the isolated polynucleotide molecules according to the present invention. Polymerases may be DNA or RNA-directed DNA polymerases. In certain embodiments, the polymerase lacks a 3' to 5' exonuclease. Suitable DNA-directed polymerases include, but are not limited to, Phi29 replicase, DNA polymerases from *Bacillus stearothermophilus*, *Thermus acquaticus*,

*Pyrococcus furiosis*, *Thermococcus litoralis*, and *Thermus thermophilus*, bacteriophage $T_4$ and $T_7$, and the *E. coli* DNA polymerase I Klenow fragment. Suitable RNA-directed DNA polymerases include, but are not limited to, the reverse transcriptase from the Avian Myeloblastosis Virus, the reverse transcriptase from the Moloney Murine Leukemia Virus, and the reverse transcriptase from the Human Immunodeficiency Virus-I.

In certain embodiments, processive DNA polymerases are used in the present application. In certain embodiments, processive DNA polymerases that polymerize more than 500, 1000, or 2000 nucleotides per polymerase-nucleic acid binding complex are used in the present application. Exemplary processive DNA polymerases include, but are not limited to, Phi29 DNA polymerase and Bca DNA polymerase.

In certain embodiments, the polymerase used to selectively attach a separation group to a targeting element or selectively stabilize a targeting element-separation group complex during the sequence-specific extraction may be the same as that for amplifying isolated polynucleotide molecules or fragments thereof. In certain other embodiment, different polymerases are used for selectively attaching a separation group to a targeting element or selectively stabilizing a targeting element-separation group complex during the sequence-specific extraction and for amplifying isolated polynucleotide molecules or fragments thereof.

7. Multiplexing

Similar to sequence-specific extraction, the amplification of the extracted (i.e., isolated) polynucleotide molecules can be performed using multiple primers or multiple sets of primers (e.g., generic primers, sequence-specific primers, or combination of generic primers and sequence-specific primers).

In some embodiments, multiplexing is used to amplify different regions of isolated polynucleotide molecules that comprise a same distinguishing element. For example, in certain embodiments, at least 2, 3, 4, 5, 6, 7, 8, 9, 10, 20, 30, 40, 50, 60, 70, 80, 90, 100, or more different regions of isolated polynucleotide molecules that comprise a same distinguishing element are amplified.

In certain other embodiments, multiplexing is used to simultaneously amplify isolated polynucleotide molecules that comprise different distinguishing elements. For example, in certain embodiments, at least 2, 3, 4, 5, 6, 7, 8, 9, 10, 20, 30, 40, 50, 60, 70, 80, 90, 100, or more different isolated polynucleotide molecules that comprise different distinguishing elements are amplified.

In certain embodiments, multiplexed haplotype-specific extraction can be used to target and extract different polynucleotide molecules that comprise different distinguishing elements from one DNA sample. The extracted polynucleotide molecules that comprise different distinguishing elements may be subsequent amplified by, e.g., whole genome amplification or whole DNA amplification, creating haploid samples that can theoretically be used, stored and re-amplified indefinitely. This allows for the creation of haploid or otherwise modified libraries from existing, stored, diploid specimens re-useable as the need arises to study regions that are not of interest initially.

C. Successive Rounds of Extraction and Amplification

If desired, successive extraction and amplification can be followed by an additional sequence-specific extraction and/or amplification. For example, an extracted sample can be subjected to generic amplification, followed by a second extraction, and then by a locus-specific amplification and, optionally, a further extraction, a further amplification, as so on. In certain embodiments, at least 2, 3, 4, 5, 6, 7, 8, 9, 10, 12, 14, 16, 18, 20 successive extractions and amplifications are performed.

D. Application Formats

The methods for nucleic acid isolation and amplification according to the present invention may be performed in various formats. For example, sequence-specific nucleic acid extraction and subsequent amplification (including generic, locus-specific, or biased amplification) can be performed using DNA arrays. The arrays can be made using techniques known in the art. In certain embodiments, arrays are conveniently provided on a flat surface.

Figure 4:
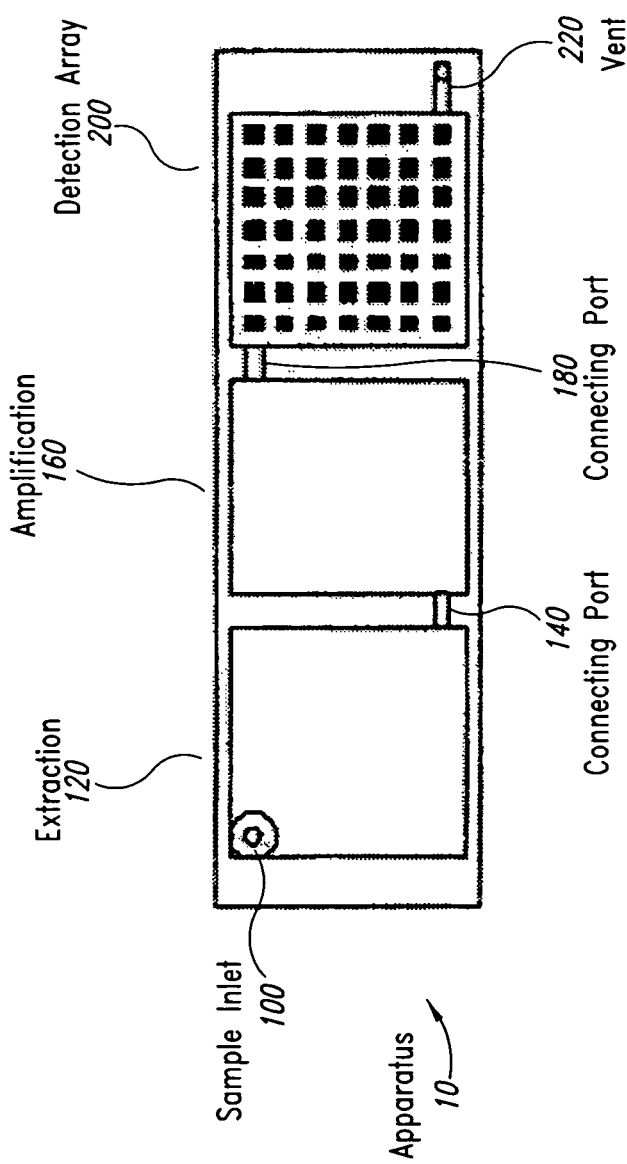
FIG. 4 is a diagram of an apparatus for integrated haplo-extraction, amplification and DNA analysis on a glass slide with a silicone cover.

Arrays can be used in an apparatus 10 for integrated sequence-specific extraction (e.g., haplotype-specific extraction), amplification and DNA analysis as shown in FIG. 4. A biological sample is introduced at inlet 100 at extraction chamber 120, where sequence-specific extraction is performed. Following the extraction, the sample is moved via a connecting port 140 into an amplification chamber 160, where the amplification step or steps are performed. Reagents and solutions can exit through a vent 220. Movement of the sample throughout the different regions of the apparatus can be facilitated by a number of methods known in the art. One exemplary mode of transport is by the use of pressure, through the movement of air or fluid in connecting channels that are controlled by external pumps or pipettes, or through controlled elastic deformation of suitable flexible components of the microstructure. For instance, a simple, reliable and convenient mode of transporting the fluid inside the apparatus is by connecting external tips to open, typically vertical ports present in the soft components of the microstructure. The tips form an airtight seal with the channels, which can be used to move fluid inside the microstructure when pumps connected to the tips are activated. The tips, or other mechanical actuators, are also able to exert pressure on regions of the microstructure that may contain sealable chambers. For example, when a tip or other actuator is positioned so as to close a vertical access port on a chamber and is then further pressed down onto the microstructure, the volume of the chamber will decrease significantly with the tip being lowered. This leads to an effective transport of fluid out of the depressed chamber into connecting regions of the microstructure. This simple procedure can repeatedly be carried out in a manual or automated format to move a sample through all regions (such as haplotype-specific extraction, amplification, detection array) of an apparatus. In the example shown here, the products of the amplification step are moved through a second connecting port 180 onto a detection array 200, where the products of the sequence-specific extraction (e.g., haplotype-specific extraction) and amplification processes are detected.

The sequence-specific extraction according to the present invention can be practiced in a fully automated embodiment by use of standard robotic liquid handling and sample preparation systems. In particular, robotic systems are commercially available that utilize magnetic beads to perform the extraction of DNA from a sample in a way that closely resembles the manual operation of such protocols. The adaptation of the method to those systems and their integration into a fully automated process line is straightforward; it requires no modification of equipment other than programming the system.

The sequence-specific extraction and subsequent amplification of the extracted polynucleotide molecules may be miniaturized to examine potentially small samples of tissue, for instance in cancer diagnosis, typing, and prognosis, and to obtain information about polymorphisms located over large contiguous regions.

In certain embodiment, the sequence-specific extraction (e.g., haplotype-specific extraction) may be performed on a single-molecular level. As an example, individual optically trapped streptavidin-coated beads can be used to capture single or numerous targeted fragments and manipulate them for instance in a microstructure (Dapprich and Nicklaus, Bioimaging 6(1):25-32, 1998). Isolated polynucleotide molecules can be transported to separate locations such as different chambers of a microstructure for further processing, such as amplification or sequence analysis (Mitra and Church, Nucleic Acids Res. 27(24):e34, 1999; Stahl et al., Nucleic Acids Res. 16(7):3025-38, 1988; Dapprich, J. Cytometry. 36(3):163-8, 1999) or removal from the microstructure. The original sample is conserved with the exception of the targeted fragments and can be re-used for subsequent extraction of different fragments.

In addition, a miniaturized and integrated device is a preferred platform in which the method can be practiced for instance for diagnostic purposes. The sequence-specific extraction can readily be adapted to standard methods and devices for miniaturized, inexpensive and integrated genotyping and sequence analysis (Hacia et al., Nat Genet. 22(2):164-7, 1999; Mitchell et al., Methods Mol Biol. 58:97-103, 1996; and Technote#303, Bangs Laboratories, Fishers, Ind.).

Sequence-specific extraction (e.g., haplotype-specific extraction) may be optionally performed on a flat support, such as on paper or on a 'dipstick'-type pregnancy test format. This support can then directly be used as the storage medium of the captured DNA and as the substrate from which further amplifications may repeatedly be generated.

E. Kits for Nucleic Acid Isolation and Amplification

In one aspect, the present invention provides kits for nucleic acid isolation and subsequent isothermal amplification. Such kits may comprise one or more of the following components: (1) one or more targeting elements (e.g., an oligonucleotide specific for extracting polynucleotide molecule that comprises a particular distinguishing element); (2) reagents for nucleic acid preparation from a biological sample (e.g., lysis buffer and neutralization buffer); (3) a separation group (e.g., a biotinylated nucleotide); (4) a substrate to which the separation group may bind (e.g., streptavidin-coated beads); (5) sequence-specific primers for amplifying polynucleotide molecules isolated by sequence-specific extraction or particular regions of the isolated polynucleotide molecules; (6) random primers; (7) dNTPs for nucleic acid amplification; (8) a polymerase for selective attachment of the separation group to the targeting element and/or for nucleic acid extension/amplification (e.g., Phi29 DNA polymerase); and (9) one or more specific probes for detecting the presence of particular sequence(s) in the amplification products (e.g., allele-specific probes).

F. Applications of Nucleic Acid Isolation and Amplification

The nucleic acid isolation and amplification methods according to the present invention have various applications. For instance, the isolated polynucleotide molecules and their amplification products may be used in a wide range of assays, including sequencing, detection of specific sequences, characterizing additional polymorphic sites, further amplifications (such as real time PCR), and mass spectrometric analysis.

In certain embodiments, the methods according to the present invention are used to identify and isolate nucleic acids containing single nucleotide polymorphisms (SNPs). Such methods facilitate performing SNP searches from pooled samples, which may require enrichment ratios of 1 in $10^6$ or $10^7$. In certain other embodiments, the methods according to the present invention are used to identify and isolate other genetic markers including restriction sites, single tandem repeats, microsatellites, and potentially epigenetic patterns such as methylation.

Figure 2C:
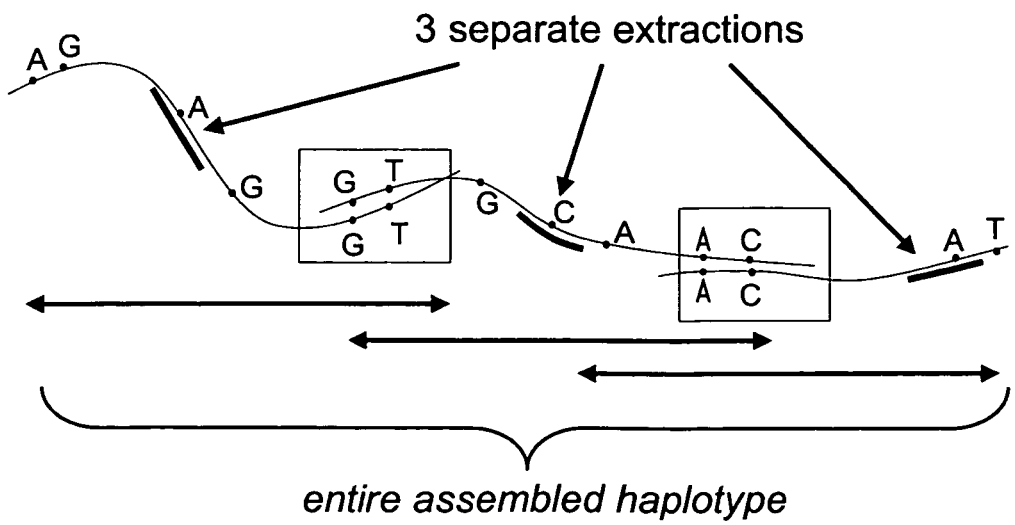
FIG. 2C is a graphical representation showing a haplotype isolated and assembled using three separate extractions.

The methods according to the present invention are not limited to pairwise comparison of two selected sites and thus allow for the correlation of an unlimited number of sites constituting a haplotype. For example, the methods of the present invention can be used to separate DNA (originating from chromosomal fragments of a sample containing multiple alleles) into fractions that contain the separated alleles only, and overlapping heterozygous regions of different fragments can be used to assemble information on co-inherited genomic regions spanning contiguous fragments (FIG. 2C). A library comprising the fractions can repeatedly be analyzed at different regions to study polymorphisms that were not classified previously, without the need for further separation of alleles.

In certain embodiments, sequence-specific extraction is used to distinguish two nearly identical sequences. In an exemplary embodiment, the method allows for separation of DNA fragments of maternal and paternal origin based on the identity of a heterozygous site so that differences between the fragments can be assessed for determining a haplotype. This ability, when coupled with standard methods commonly used for genotyping, permits rapid large-scale and cost-effective haplotyping of individuals, which can significantly reduce the size and decrease the duration of genetic profiling studies by focusing on the analysis of rare events, such as therapeutic non-responders or adversely affected individuals.

In certain embodiments where haplotype-specific extraction and amplification are used to determine a haplotype for an individual, the haplotypes can be selected based on a preselected set of genes or loci. For example, 1-500, or 5-250, 10-200, 20-100, 25-75, or about 50 sites can be selected. Sites can be, e.g., regions in the genome suspected to be involved with a particular trait.

For example, in certain embodiments, a haplotype is determined first for individuals that are affected with a particular disease or condition, and any conserved genetic patterns are identified. The patterns are then compared to a control group (i.e., a group not showing the disease or condition) to reveal potential associations. The same holds for the identification of tissue types or classes of disease, for instance in molecular-based classification of certain types of cancers.

In addition, haplotype-specific extraction allows the unambiguous identification of tissue type and can detect abnormalities potentially associated with certain diseases or conditions, such as loss of heterozygosity, inversions, deletions, duplications or translocations. In other embodiments, retrospective studies are performed to identify genetic relationships for responsiveness (both positive and adverse) to a therapeutic treatment (such as a pharmaceutical, surgical, or radiation-based treatment). Results from these studies can be used to determine the likelihood that patients will respond to, or have an adverse reaction to, the given therapeutic treatment.

The nucleic acid isolation and amplification methods according to the present invention extend the directly achievable linkage distance per extraction and increase the robustness of subsequent manipulations by increasing amount of available template. In certain embodiments, the linkage distance per extraction is at least about 10, 20, 50, 70, 100, 150, 300, 500, or 800 Kb, or no less than about 1 Mb.

In certain embodiments, the combination of haplotype-specific extraction with whole DNA amplification is used for tissue-typing because it permits the unambiguous typing of potentially recalcitrant diploid samples with allele pair combinations that fail to be resolved by conventional sequence-based typing (SBT) or sequence-specific oligonucleotide probes (SSOP). It also permits the typing of haplo-separated samples with multiple polymorphisms over large linkage distances that may otherwise fail to amplify properly with locus-specific amplification alone.

Additional applications of the present invention include facilitating classification of cancers, ongoing monitoring genetic changes in the tumor as well as in the host, predicting efficacy of oncology drugs, enriching for tumor DNA or viral nucleic acids from mixed, contaminated or forensic samples, monitoring minimal residual diseases and other diseases (e.g., cancer and HIV), diagnosing human diseases, determining predispositions to human diseases (including metabolic disease, cancer typing, diagnosis, and prognosis), analyzing organelle DNA (mitochondrial and chloroplast) and plant traits, and facilitating drug discovery and evolutionary studies (e.g., tracking of disease evolution).

The invention will be further illustrated in the following non-limiting examples.

EXAMPLE

Figure 3:
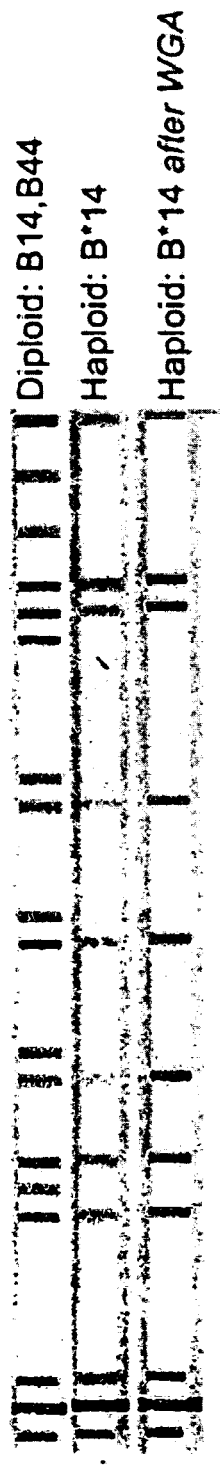
FIG. 3 is a sequence-specific oligonucleotide probe (SSOP) signal generated for a diploid control sample ("Diploid: B14, B44") and a haplo-separated sample before ("Haploid: B*14") and after whole-DNA amplification ("Haploid: B*14 after WGA").

The Phi29 replicase/GenomiPhi kit (Amersham Biosciences) was used to amplify haplo-separated genomic DNA after haplotype-specific extraction. The resulting amplified DNA, when typed by sequence-specific oligonucleotide probes (SSOP; Innogenetics), was still haploid and had essentially no visible residual component of non-targeted alleles. The SSOP signal generated for a haplo-separated sample is considerably stronger than for a diploid control sample (FIG. 3).

Commercially available primers and test strips (Innogenetics/Murex, Dartford, UK) were used to perform generic amplifications of the HLA-B exons 1-3 after haplo-separating diploid samples by haplotype-specific extraction. The typing of each sample consists of two strips, both of which are shown in FIG. 3 as obtained directly from the scanned strips. The samples were amplified from 1 µl of starting material (haplo-extracted DNA on beads). All lines expected for the two haploid fractions are present both before and after whole-genome amplification. None of the lines expected for other non-targeted alleles are present, even after whole-DNA amplification.

These results demonstrate the compatibility of haplotype-specific extraction with whole DNA amplification.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for amplifying a polynucleotide molecule of interest or a fragment thereof, comprising:
   (a) isolating a polynucleotide molecule from a nucleic acid population using an immobilizable separation group to provide an isolated polynucleotide molecule, and
   (b) isothermally amplifying the isolated polynucleotide molecule or a fragment thereof, wherein
      (i) the amplification is a sequence-biased amplification which is defined as a hybrid of generic amplification and sequence-specific amplification performed in the presence of both random primers and sequence-specific primers, or
      (ii) the amplification is a sequence-specific amplification performed in the presence of center-specific primers and end-specific primers.

2. The method of claim 1 wherein
   (A) the nucleic acid population comprises the polynucleotide molecule of interest,
   (B) one strand of the polynucleotide molecule comprises a target nucleic acid sequence and a distinguishing element,
   (C) the target nucleic acid sequence is within 100 nucleotides of the distinguishing element in the one strand of the polynucleotide molecules, and
   (D) step (a) comprises:
      (i) contacting the nucleic acid population with a targeting element that binds specifically to the target nucleic acid sequence in the polynucleotide molecule,
      (ii) selectively attaching the immobilizable separation group to the targeting element bound to the target nucleic acid sequence in the polynucleotide molecule to form a targeting element-separation group complex,
      (iii) immobilizing to a substrate via the separation group the targeting element-separation group complex to which the target nucleic acid sequence in the polynucleotide molecule is bound, and
      (iv) removing the immobilized targeting element-separation group complex to which the target nucleic acid sequence in the polynucleotide molecule is bound, thereby isolating the polynucleotide molecule from the nucleic acid population.

3. The method of claim 2 wherein the polynucleotide molecule of interest is a genomic DNA molecule.

4. The method of claim 2 wherein the target nucleic acid sequence is located immediately 3' to the distinguishing element in the one strand of the polynucleotide molecule.

5. The method of claim 2 wherein the targeting element comprises an oligonucleotide.

6. The method of claim 2 wherein the separation group comprises an immobilizable nucleotide.

7. The method of claim 6 wherein the immobilizable nucleotide is a terminating nucleotide.

8. The method of claim 6 wherein the immobilizable nucleotide is a non-terminating nucleotide.

9. The method of claim 2 wherein the distinguishing element is a polymorphic sequence.

10. The method of claim 2 wherein the distinguishing element is a single nucleotide polymorphism.

11. The method of claim 2 wherein
   (1) the targeting element comprises an oligonucleotide,
   (2) the separation group comprises an immobilizable nucleotide, and
   (3) the separation group is attached to the targeting element by extending the oligonucleotide in the presence of the immobilizable nucleotide, thereby forming an extension product that comprises the immobilizable nucleotide.

12. The method of claim 11 wherein
   (4) the 3' terminus of the oligonucleotide is complementary to the distinguishing element or a portion thereof in the polynucleotide molecule,
   (5) the immobilizable nucleotide is non-terminating, and
   (6) the extension product comprises multiple separation groups.

13. The method of claim 11 wherein
   (4) the target nucleic acid sequence is immediately 3' to the distinguishing element, and
   (5) the immobilizable nucleotide is terminating and complementary to the distinguishing element or a portion thereof.

14. The method of claim 2 wherein the distinguishing element is haplotype-specific.

15. The method of claim 2 wherein the distinguishing element is locus-specific.

16. The method of claim 2 further comprising dissociating the isolated polynucleotide molecule from the substrate prior to step (b).

17. The method of claim 1 wherein
   (A) the nucleic acid population comprises the polynucleotide molecule of interest,
   (B) one strand of the polynucleotide molecule comprises a target nucleic acid sequence and a distinguishing element,
   (C) the target nucleic acid sequence is within 100 nucleotides of the distinguishing element in the one strand of the polynucleotide molecule, and (D) step (a) comprises:
  (i) contacting the nucleic acid population with a targeting element-separation group complex, wherein the targeting element-separation group complex binds specifically to the target nucleic acid sequence in the polynucleotide molecule,
  (ii) selectively stabilizing the binding of the targeting element-separation group complex to the target nucleic acid sequence in the polynucleotide molecule,
  (iii) immobilizing to a substrate via the separation group the stabilized targeting element-separation group complex to which the target nucleic acid sequence in the polynucleotide molecule is bound, and
  (iv) removing the immobilized stabilized targeting element-separation group complex to which the target nucleic acid sequence in the polynucleotide molecule is bound, thereby isolating the polynucleotide molecule from the nucleic acid population.

18. The method of claim 17 wherein
  (1) the targeting element of the targeting element-separation group complex comprises an oligonucleotide, and
  (2) the 3' terminus of the oligonucleotide is complementary to the distinguishing element or a portion thereof in the polynucleotide.

19. The method of claim 17 further comprising dissociating the isolated polynucleotide molecule from the substrate prior to step (b).

20. The method of claim 1 wherein the polynucleotide molecule is at least about 10 kb in length.

21. The method of claim 1 wherein the random primers are about 2 kb apart from their neighboring primers.

22. The method of claim 1 further comprising:
  (c) characterizing one or more polymorphic sites in the amplified polynucleotide molecule or fragment thereof, and optionally
  (d) assembling information of the characterized sites.

23. The method of claim 1 wherein the sequence-biased amplification is a locus-biased amplification which is defined as a hybrid of generic amplification and locus-specific amplification and is performed in the presence of both random primers and locus-specific primers.

24. The method of claim 23 wherein the locus-specific primers bind to a common sequence within, or flanking, the locus shared by all or a majority of the alleles occupying the locus.

25. The method of claim 24 wherein the sequence flanking the locus is located outside the locus but the distance between the sequence flanking the locus and the nearby terminus of the locus is within 500 nucleotides.

26. The method of claim 1 wherein in the sequence-biased amplification the sequence-specific primers are end-specific primers.

27. The method of claim 26 wherein the end-specific primers anneal to the isolated polynucleotide molecule or the fragment thereof within 500 nucleotides from an end of the isolated polynucleotide molecule or the fragment thereof.

28. The method of claim 1 wherein in the sequence-specific amplification the center-specific primers are degenerate primers whose sequence has several possible bases at certain positions.

29. The method of claim 1 wherein the end-specific primers anneal to the isolated polynucleotide molecule or the fragment thereof within 500 nucleotides from an end of the isolated polynucleotide molecule or the fragment thereof.

30. A method for amplifying multiple polynucleotide molecules of interest from a population of nucleic acid molecules, comprising:
  (a) isolating multiple polynucleotide molecules from a nucleic acid population using one or more immobilizable separation groups to provide isolated polynucleotide molecules of interest, and
  (b) isothermally amplifying the isolated polynucleotide molecules or fragments thereof, wherein
    (i) the amplification is a sequence-biased amplification which is defined as a hybrid of generic amplification and sequence-specific amplification performed in the presence of both random primers and sequence-specific primers, or
    (ii) the amplification is a sequence-specific amplification performed in the presence of center-specific primers and end-specific primers.

31. The method of claim 30 wherein step (a) comprises:
(A) contacting a nucleic acid population that comprises multiple polynucleotide molecules of interest with multiple targeting elements so that each targeting element binds specifically to a target nucleic acid sequence of its corresponding polynucleotide molecule, wherein
  (i) the target nucleic acid sequence is located within 100 nucleotides of a distinguishing element in one strand of the polynucleotide molecule, and
  (ii) the distinguishing element distinguishes the polynucleotide molecule from another nucleic acid molecule that is nearly identical to the polynucleotide molecule,
(B) selectively attaching separation groups to the multiple targeting elements bound to the target nucleic acid sequences of corresponding polynucleotide molecules to form targeting element-separation group complexes,
(C) immobilizing to substrate(s) via the separation groups the targeting element-separation group complexes to which the target nucleic acid sequences in the polynucleotide molecules are bound, and
(D) removing the immobilized targeting element-separation group molecules are bound to isolate the polynucleotide molecules from the population of nucleic acid molecules.

32. The method of claim 31 wherein different separation groups are attached to different targeting elements.

33. The method of claim 31 wherein identical separation groups are attached to different targeting elements.

34. The method of claim 31 wherein at least three different polynucleotide molecules of interest are isolated.

35. The method of claim 30 wherein step (a) comprises:
(A) contacting a nucleic acid population that comprises multiple polynucleotide molecules of interest with multiple targeting elements to which separation groups are attached so that each targeting element binds specifically to a target nucleic acid sequence of its corresponding polynucleotide molecule, wherein
  (i) the target nucleic acid sequence is located within 100 nucleotides of a distinguishing element in one strand of the polynucleotide molecule, and
  (ii) the distinguishing element distinguishes the polynucleotide molecule from another nucleic acid molecule that is nearly identical to the polynucleotide molecule,
(B) selectively stabilizing the binding of the targeting elements to the target nucleic acid sequences of their corresponding polynucleotide molecules to form stabilized targeting element-separation group complexes to which the target nucleic acid sequences in the polynucleotide molecules are bound,
(C) immobilizing to substrate(s) via the separation groups the targeting element-separation group complexes to which the target nucleic acid sequences in the polynucleotide molecules are bound, and
(D) removing the immobilized targeting element-separation group complexes to which the target nucleic acid sequences in the polynucleotide molecules are bound to isolate the polynucleotide molecules from the population of nucleic acid molecules.

36. A method for amplifying a genomic DNA molecule of interest or a fragment thereof, wherein the genomic DNA molecule of interest comprises a polymorphic sequence, comprising:
(a) contacting a genomic DNA population that comprises the genomic DNA molecule of interest with an oligonucleotide, wherein
  (i) the oligonucleotide comprises a sequence at least substantially complementary to a target nucleic acid sequence in one strand of the genomic DNA molecule of interest,
  (ii) the target nucleic acid sequence is located immediately 3' to the polymorphic sequence in the one strand of the genomic DNA molecule of interest, and
  (iii) the 3' portion of the oligonucleotide is complementary to the polymorphic sequence or a portion thereof when annealing to the one strand of the genomic DNA molecule of interest,
(b) extending the oligonucleotide in the presence of an immobilizable nucleotide using the one strand of the genomic DNA molecule of interest to which the oligonucleotide anneals as a template to provide an extension product,
(c) immobilizing to a substrate via the immobilizable nucleotide the extension product to which the genomic DNA molecule of interest is bound,
(d) removing the immobilized extension product to which the genomic DNA molecule of interest is bound to thereby isolate the genomic DNA molecule of interest from the genomic DNA population,
(e) optionally elute the genomic DNA molecule of interest from the substrate, and
(f) isothermally amplifying the isolated or eluted genomic DNA molecule of interest or a fragment thereof, wherein
  (i) the amplification is a sequence-biased amplification which is defined as a hybrid of generic amplification and sequence-specific amplification performed in the presence of both random primers and sequence-specific primers, or
  (ii) the amplification is a sequence-specific amplification performed in the presence of center-specific primers and end-specific primers.

* * * * *

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Example nucleic acid target molecule with an
      intervening sequence between the binding location
      of the targeting element and the polymorphic site
      distinguishing the two alleles

<400> SEQUENCE: 1
gattaccaaa aattc                                                      15

<210> SEQ ID NO 2
<211> LENGTH: 15
<212> TYPE: DNA
<213> ORGANISM: Artificial Sequence
<220> FEATURE:
<223> OTHER INFORMATION: Example nucleic acid target molecule with an
      intervening sequence between the binding location
      of the targeting element and the polymorphic site
      distinguishing the two alleles

<400> SEQUENCE: 2
gattaccaaa aagtc                                                      15

<210> SEQ ID NO 3
<211> LENGTH: 24
<212> TYPE: DNA
<213> ORGANISM: Artificial Sequence
<220> FEATURE:
```

```
<223> OTHER INFORMATION: Oligonucleotide primer

<400> SEQUENCE: 3
ttagtgctga acaagtagat caga                                      24

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 4
gtatattcca agatccatta gcag                                      24
```